United States Patent
Woehr et al.

(10) Patent No.: US 9,289,237 B2
(45) Date of Patent: Mar. 22, 2016

(54) SPRING CLIP SAFETY IV CATHETER

(71) Applicant: B. BRAUN MELSUNGEN AG, Melsungen (DE)

(72) Inventors: Kevin Woehr, Felsberg (DE); Manfred Orth, Vellmar (DE); Mark Wynkoop, Coopersberg (DE); Matthew Kohler, East Greenville, PA (US)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 14/160,349

(22) Filed: Jan. 21, 2014

(65) Prior Publication Data

US 2014/0135701 A1    May 15, 2014

Related U.S. Application Data

(63) Continuation of application No. 13/656,980, filed on Oct. 22, 2012, now Pat. No. 8,647,313, which is a continuation of application No. 13/311,361, filed on Dec. 5, 2011, now Pat. No. 8,382,721, which is a (Continued)

(51) Int. Cl.
*A61M 5/00* (2006.01)
*A61B 17/34* (2006.01)
(Continued)

(52) U.S. Cl.
CPC ............ *A61B 17/3494* (2013.01); *A61M 5/158* (2013.01); *A61M 5/3273* (2013.01);
(Continued)

(58) Field of Classification Search
CPC .......... A61M 5/3273; A61M 25/0618; A61M 2005/325; A61M 25/0606; A61M 25/0625

USPC ............ 604/263, 166, 168, 110, 164.01–164, 604/198
See application file for complete search history.

(56) References Cited

U.S. PATENT DOCUMENTS 3,610,240 A    10/1971  Harautuneian
3,904,033 A     9/1975  Haerr
(Continued)

FOREIGN PATENT DOCUMENTS

EP    0 352 928 B1    12/1992
EP    0 554 841 A1     8/1993
(Continued)

OTHER PUBLICATIONS

Notice of Allowance mailed Nov. 12, 2013 from related U.S. Appl. No. 13/656,980.
(Continued)

*Primary Examiner* — Phillip Gray
(74) *Attorney, Agent, or Firm* — Klein, O'Neill & Singh, LLP

(57) ABSTRACT

A safety IV catheter includes a unitary, resilient needle guard received in a catheter hub. The needle guard includes a proximal arm or wall that includes an opening through which a needle passes for axial movement. When the needle is retracted from the catheter, it releases the force that had previously prevented movement of the needle guard within the catheter hub. This in turn causes the needle guard to snap into a position in which it is clamped onto the needle shaft and in which its distal wall blocks access to the needle tip. In this condition, the spring needle guard and needle can be removed from the catheter hub. A slot or crimp may be formed in the needle shaft that engages with the needle guard after the protected needle and needle guard are removed from the catheter hub, thereby to prevent removal of the protected needle from the needle guard.

25 Claims, 18 Drawing Sheets

Related U.S. Application Data continuation of application No. 10/734,931, filed on Dec. 12, 2003, now Pat. No. 8,211,070, which is a continuation-in-part of application No. 10/445,166, filed on May 23, 2003, now Pat. No. 7,264,613, which is a continuation of application No. 09/638,641, filed on Aug. 14, 2000, now Pat. No. 6,616,630, which is a continuation-in-part of application No. 09/183,697, filed on Oct. 30, 1998, now Pat. No. 6,287,278, which is a continuation-in-part of application No. 09/097,170, filed on Jun. 12, 1998, now Pat. No. 6,117,108, which is a continuation-in-part of application No. 08/915,148, filed on Aug. 20, 1997, now abandoned.

(51) Int. Cl.
  *A61M 5/158* (2006.01)
  *A61M 5/32* (2006.01)
  *A61M 25/06* (2006.01)

(52) U.S. Cl.
  CPC ....... *A61M25/0606* (2013.01); *A61M 25/0618* (2013.01); *A61M 25/0625* (2013.01); *A61M 25/0631* (2013.01); *A61M 5/3275* (2013.01); *A61M 2005/325* (2013.01); *A61M 2005/3247* (2013.01)

(56) References Cited

U.S. PATENT DOCUMENTS

| | | | |
|---|---|---|---|
| 4,160,450 A | 7/1979 | Doherty | |
| 4,250,881 A | 2/1981 | Smith | |
| 4,725,267 A | 2/1988 | Vaillancourt | |
| 4,735,618 A | 4/1988 | Hagen | |
| 4,747,831 A | 5/1988 | Kulli | |
| 4,790,828 A | 12/1988 | Dombrowski et al. | |
| 4,795,432 A | 1/1989 | Karczmer | |
| 4,846,809 A | 7/1989 | Sims | |
| 4,929,241 A | 5/1990 | Kulli | |
| 4,944,725 A | 7/1990 | McDonald | |
| 4,952,207 A | 8/1990 | Lemieux | |
| 4,964,854 A * | 10/1990 | Luther ................ | A61M 5/3273 604/166.01 |
| 4,978,344 A | 12/1990 | Dombrowski et al. | |
| 4,994,041 A | 2/1991 | Dombrowski et al. | |
| 5,049,136 A | 9/1991 | Johnson | |
| 5,051,109 A | 9/1991 | Simon | |
| 5,053,017 A | 10/1991 | Chamuel | |
| 5,053,107 A | 10/1991 | Barber, Jr. | |
| 5,085,648 A | 2/1992 | Purdy et al. | |
| 5,120,320 A | 6/1992 | Fayngold | |
| 5,120,321 A | 6/1992 | Oksman et al. | |
| 5,126,090 A | 6/1992 | Egolf et al. | |
| 5,135,504 A | 8/1992 | McLees | |
| 5,147,327 A | 9/1992 | Johnson | |
| 5,171,229 A | 12/1992 | McNeil et al. | |
| 5,183,468 A | 2/1993 | McLees | |
| 5,215,525 A * | 6/1993 | Sturman ........... | A61M 25/0631 604/164.08 |
| 5,215,528 A | 6/1993 | Purdy et al. | |
| 5,217,438 A | 6/1993 | Davis et al. | |
| RE34,416 E | 10/1993 | Lemieux | |
| 5,279,570 A | 1/1994 | Dombrowski et al. | |
| 5,279,591 A | 1/1994 | Simon | |
| 5,300,045 A | 4/1994 | Plassche, Jr. | |
| 5,312,371 A | 5/1994 | Dombrowski et al. | |
| 5,322,517 A | 6/1994 | Sircom et al. | |
| 5,328,482 A | 7/1994 | Sircom et al. | |
| 5,334,158 A | 8/1994 | McLees | |
| 5,344,408 A | 9/1994 | Partika | |
| 5,348,544 A | 9/1994 | Sweeney et al. | |
| 5,370,623 A | 12/1994 | Kreamer | |
| 5,419,766 A | 5/1995 | Chang et al. | |
| 5,423,766 A | 6/1995 | Di Cesare | |
| 5,458,658 A | 10/1995 | Sircom | |
| 5,501,675 A | 3/1996 | Erskine | |
| 5,549,570 A | 8/1996 | Rogalsky | |
| 5,558,651 A | 9/1996 | Crawford et al. | |
| 5,584,809 A | 12/1996 | Gaba | |
| 5,584,810 A | 12/1996 | Brimhall | |
| 5,584,818 A | 12/1996 | Morrison | |
| 5,599,310 A | 2/1997 | Bogert | |
| 5,601,536 A | 2/1997 | Crawford et al. | |
| 5,611,781 A | 3/1997 | Sircom et al. | |
| 5,662,610 A | 9/1997 | Sircom | |
| 5,697,907 A | 12/1997 | Gaba | |
| 5,718,688 A | 2/1998 | Wozencroft | |
| 5,738,665 A | 4/1998 | Caizza et al. | |
| 5,843,048 A | 12/1998 | Gross | |
| 5,879,337 A | 3/1999 | Kuracina et al. | |
| 5,882,337 A | 3/1999 | Bogert et al. | |
| 6,001,080 A | 12/1999 | Kuracina et al. | |
| 6,004,294 A | 12/1999 | Brimhall et al. | |
| 6,117,108 A | 9/2000 | Woehr et al. | |
| 6,224,569 B1 | 5/2001 | Brimhall | |
| 6,287,278 B1 | 9/2001 | Woehr et al. | |
| 6,443,929 B1 | 9/2002 | Kuracina et al. | |
| 6,616,630 B1 | 9/2003 | Woehr et al. | |
| 6,652,486 B2 | 11/2003 | Bialecki et al. | |
| 6,749,588 B1 | 6/2004 | Howell et al. | |

FOREIGN PATENT DOCUMENTS

| | | |
|---|---|---|
| EP | 0 588 470 A1 | 3/1994 |
| EP | 0 750 915 A2 | 1/1997 |
| EP | 0 750 916 A2 | 1/1997 |
| EP | 0 747 085 B2 | 4/2003 |
| EP | 1 003 588 B1 | 11/2004 |
| EP | 1 180 381 B1 | 12/2005 |
| JP | 9-99068 | 4/1997 |
| JP | 9-99073 | 4/1997 |
| MX | 209311 | 10/1997 |
| WO | WO 90/08564 | 8/1990 |
| WO | WO 97/42989 | 11/1997 |
| WO | WO 99/08742 | 2/1999 |
| WO | WO 00/69501 | 11/2000 |

OTHER PUBLICATIONS

Office Action mailed Mar. 15, 2013 from related U.S. Appl. No. 13/656,980.
Notice of Allowance mailed Oct. 16, 2012 from related U.S. Appl. No. 13/311,361.
Office Action mailed Apr. 2, 2012 from related U.S. Appl. No. 13/311,361.
Final Office Action mailed Apr. 16, 2009 from related U.S. Appl. No. 11/609,772.
Office Action mailed Sep. 29, 2008 from related U.S. Appl. No. 11/609,772.
Final Office Action mailed Mar. 18, 2009 from related U.S. Appl. No. 11/537,368.
Office Action mailed Sep. 26, 2008 from related U.S. Appl. No. 11/537,368.
Office Action mailed Dec. 26, 2008 from related U.S. Appl. No. 11/678,565.
Office Action mailed Jan. 25, 2006 from related U.S. Pat. No. 7,125,397.
Notice of Allowance mailed Jun. 28, 2006 from related U.S. Pat. No. 7,125,397.
Corrected Notice of Allowability mailed Oct. 4, 2006 from related U.S. Pat. No. 7,125,397.
Response to 312 Amendment mailed Jan. 3, 2007 from related U.S. Pat. No. 7,214,211.
Notice of Allowance mailed Sep. 19, 2006 from related U.S. Pat. No. 7,214,211.
Advisory Action mailed May 5, 2006 from related U.S. Pat. No. 7,214,211.
Final Office Action mailed Apr. 4, 2006 from related U.S. Pat. No. 7,214,211.

(56) References Cited

OTHER PUBLICATIONS

Office Action mailed Jul. 28, 2005 from related U.S. Pat. No. 7,214,211.
Office Action mailed May 18, 2005 from related U.S. Pat. No. 7,214,211.
Office Action mailed Nov. 16, 2006 from related U.S. Pat. No. 7,214,211.
Office Action mailed Jan. 3, 2007 from related U.S. Pat. No. 7,214,211.
Office Action mailed Dec. 5, 2008 from related U.S. Appl. No. 11/326,780.
Office Action mailed Oct. 23, 2007 from related U.S. Appl. No. 10/734,931.
Final Office Action mailed Apr. 8, 2008 from related U.S. Appl. No. 10/734,931.
Examiner's Answer mailed Dec. 30, 2008 from related U.S. Appl. No. 10/734,931.
Office Action mailed Aug. 13, 2004 from related U.S. Pat. No. 7,264,613.
Office Action mailed Dec. 1, 2004 from related U.S. Pat. No. 7,264,613.
Final Office Action mailed May 13, 2005 from related U.S. Pat. No. 7,264,613.
Office Action mailed Feb. 10, 2006 from related U.S. Pat. No. 7,264,613.
Final Office Action mailed Nov. 17, 2006 from related U.S. Pat. No. 7,264,613.
Advisory Action mailed Dec. 27, 2006 from related U.S. Pat. No. 7,264,613.
Notice of Allowance mailed Feb. 7, 2007 from related U.S. Pat. No. 7,264,613.
Office Action mailed Sep. 18, 2002 from related U.S. Pat. No. 6,616,630.
Office Action mailed Dec. 31, 2002 from related U.S. Pat. No. 6,616,630.
Notice of Allowance mailed Apr. 28, 2003 from related U.S. Pat. No. 6,616,630.
Office Action mailed Sep. 10, 1999 from related U.S. Pat. No. 6,287,278.
Office Action mailed Nov. 22, 1999 from related U.S. Pat. No. 6,287,278.
Final Office Action mailed Dec. 11, 2000 from related U.S. Pat. No. 6,287,278.
Final Office Action mailed Feb. 14, 2001 from related U.S. Pat. No. 6,287,278.
Notice of Allowance mailed Jun. 14, 2001 from related U.S. Pat. No. 6,287,278.
Office Action mailed Apr. 22, 1999 from related U.S. Pat. No. 6,117,108.
Final Office Action mailed Sep. 14, 1999 from related U.S. Pat. No. 6,117,108.
Notice of Allowance mailed Feb. 8, 2000 from related U.S. Pat. No. 6,117,108.
Office Action mailed Apr. 30, 1998 from related U.S. Appl. No. 08/915,148.
Office Action mailed Jul. 20, 1998 from related U.S. Appl. No. 08/915,148.
Office Action dated Jul. 28, 2005 from U.S. Appl. No. 10/455,166, filed May 23, 2003.
Related to U.S. Appl. No. 11/326,780, filed Jan. 5, 2006, which is a continuation of U.S. Appl. No. 10/734,931, filed Dec. 12, 2003, which is a CIP of U.S. Appl. No. 10/445,166.
Complaint for Case No. 09 CV 00347, filed May 13, 2009, District of Delaware, United States District Court (40 pages).
B. Braun Melsungen AG's Response to Opposition of Communication dated Sep. 26, 2005 and two (2) Notices of Opposition of Termuno; Response to Opposition dated Mar. 24, 2006, filed by Klingseisen of Zumstein & Klingseisen, including supporting documents (39 pages).
Australian Patent No. 783650, Published Feb. 21, 2002, Applicant's B. Braun Melsungen AG, entitled "Intravenous Catheter Device" (23 pages).
Statutory Declaration of Joseph J. Chang, Executed and Notarized on Jan. 9, 2007, In the matter of Australian Patent Acceptance No. 783650 and in the Matter of Opposition thereto by Smiths Medical ASD, Inc. (16 pages).
Australian Statement of Grounds and Particulars of Opposition from Medex, Inc., Spruson & Ferguson dated May 17, 2006 regarding Patent Application No. 783650 (2 pages).
Notice of Opposition to a European Patent; Opponents Smiths Medical ASD, Inc.; to B. Braun Melsungen AG for Opposed Patent No. 1 180 381; Application No. 01 109 231.9; dated Sep. 27, 2006 (25 pages).
Notice of Opposition to a European Patent; Opponent Terumo Corporation; to B. Braun Melsungen AG for Opposed Patent No. EP 1 003 588 B1; Application No. 98 948 843.2; dated Aug. 16, 2005 (17 pages).
Notice of Opposition to a European Patent; Opponent Medex, Inc.; to B. Braun Melsungen AG for Opposed Patent No. 1 003 588; Application No. 98 948843.2; dated Aug. 17, 2005 (26 pages).
Affidavit of Joseph J. Chang; In the Court of the Commissioner of Patents for the Republic of South Africa; Case No. Patent 2001/3937; In the matter between: B. Braun Melsungen AG (First Applicant), B. Braun Medical (Proprietary) Limited (Second Applicant) and Specialised Systems Electro Medical (Proprietary) Limited (Respondent dated May 6, 2004 (84 pages).
Supplementary Answering Affidavit of Dennis Bialecki; In the Court of the Commissioner of Patents for the Republic of South Africa; Case No. Patent 2001/3937; In the matter between: B. Braun Melsungen AG (First Applicant), B. Braun Medical (Proprietary) Limited (Second Applicant) and Specialised Systems Electro Medical (Proprietary) Limited (Respondent) dated Sep. 15, 2005 (35 pages).
Replying Affidavit of Kevin Woehr; In the Court of the Commissioner of Patents for the Republic of South Africa; Case No. Patent 2001/3937; In the matter between: B. Braun Melsungen AG (First Applicant), B. Braun Medical (Proprietary) Limited (Second Applicant) and Specialised Systems Electro Medical (Proprietary) Limited (First Respondent) dated Oct. 19, 2005 (34 pages).
Affidavit of Kevin Woehr; In the Court of the Commissioner of Patents for the Republic of South Africa; Case No. Patent 2001/3937; In the matter between: B. Braun Melsungen AG (First Applicant), B. Braun Medical (Proprietary) Limited (Second Applicant) and Specialised Systems Electro Medical (Proprietary) Limited (First Respondent) and the Registrar of Patents (Second Respondent) dated Jun. 4, 2004 (16 pages).
Amended Sheet of Claims for South African Serial No. 2001/3937; filed Oct. 22, 2003; Claims 1-12 (8 sheets) and Figures 1-10 (3 sheets) (11 sheets total).
Affidavit of Dennis Bialecki; In the Court of the Commissioner of Patents for the Republic of South Africa; Case No. Patent 2001/3937; In the matter between: B. Braun Melsungen AG (First Applicant), B. Braun Medical (Proprietary) Limited (Second Applicant) and Specialised Systems Electro Medical (Proprietary) Limited (First Respondent), The Registrar of Patents (Second Respondent) and Medex Inc. (Third Respondent) dated Oct. 13, 2004 (33 pages).
Affidavit of Kevin Woehr; In the Court of the Commissioner of Patents for the Republic of South Africa; Case No. Patent 2001/3937; In the matter between: B. Braun Melsungen AG (First Applicant), B. Braun Medical (Proprietary) Limited (Second Applicant) and Specialised Systems Electro Medical (Proprietary) Limited (First Respondent), The Registrar of Patents (Second Respondent) and Medex Inc. (Third Respondent) dated Nov. 22, 2004 (38 pages).
In the Court of the Commissioner of Patent for the Republic of South Africa, entitled "Supplemental Answering Affidavit," Case No. Patent 2001/3937, B. Braun Melsungen AG (First Applicant) and B. Braun Medical (Proprietary) Limited (Second Applicant) and Specialised Systems Electro Medical (Proprietary) Limited (Respondent), in regards patent of addition 2001/3937 and an application for infringement thereof, Affidavit of Dennis Bialecki, dated an signed Sep. 1, 2005 (36 pages).

(56) References Cited

OTHER PUBLICATIONS

Letter to Commissioner, dated Aug. 18, 2006, U.S. Appl. No. 10/445,166, filed May 23, 2003, entitled "Spring Clip Safety IV Catheter," Confirmation No. 1659, executed by Tom H. Dao, Registration No. 44,641 (3 pages).
Administrative Declaration of Nullity requested by a Counterclaim against Patent No. 218,845, entitled "Spring Clip as Needle Tip Protection for an IV Safety Catheter," *B. Braun Melsungen AG* vs. *Medex De Mexico, S.A. De C.V.* (58 pages).
Nullity of the Patent of invention PI9812128-6, filed on Aug. 18, 1998 and issued on Mar. 30, 2004, In the name of B. Braun Melsungen AG under the Title "IV Catheter and Catheter Device," Signed by Antonio M.P. Arnaud, Sao Paulo, Sep. 29, 2004 (21 pages).
Response to the Request of Administration Nullity of the Patent P19812128-6, dated Mar. 30, 2004, Patentee: B. Braun Melsungen AG, entitled "Catheter and Catheter Device," Rio de Janeiro, Feb. 28, 2005, Momsen, Leonardos& CIA (8 pages).
Technical Report Published on Jul. 26, 2005, Brazilian Patent No. P19812128-6, PCT/EP98/05231, filed Aug. 18, 1998, Applicant: B. Braun Melsungen AG, Classification: A61M 25/06; A61M 5/32, Granting Date: Mar. 30, 2004, entitled "IV Catheter and Catheter Device," dated Jun. 29, 2005, In agreement, signed by Leila Freire Falcone, Coordinator of the Appeal and Administrative Nullity Section (4 pages).
Response to the Technical Report Regarding the Request for Administrative Nullity of the Patent PI9812128-6, dated Mar. 30, 2004, Patentee: B. Braun Melsungen AG, entitled "IV Catheter and Catheter Device," Rio de Janeiro, Sep. 26, 2005, Momsen, Leonardos & CIA (9 pages).
Amended Passages in the Specification, Claims as presented on Jan. 19, 2003, showing the pending claims at issue in the Brazilian nullity action (5 pages).
Information Disclosure Statement (IDS) of Reissue Application U.S. Pat. No. 6,652,486 B2, Issued Nov. 25, 2006, including Substitute Form PTO-1449. This IDS was cited for U.S. Appl. No. 11/013,289 (6 pages).
Japanese Publication No. P2002-85558A, Publication Date: Mar. 26, 2002, Filing Date: Sep. 19, 2000, including English Translation.
Prior art drawings of B. Braun Medical Inc., listed as "Ga. Spring Clip Detail for Introcan Catheter", dated Apr. 20, 1999, ref. No. PRE-670, on sale as early as Mar. 2000 (3 sheets).
Prior art drawing by B. Braun Medical, Inc., listed as "Ga. Spring Clip Detail for Introcan Catheter", dated Jun. 15, 1999, ref. No. PRE-671, on sale as early as Mar. 2000 (1 sheet).
Stipulated Protective Order for Case No. 09 CV 00347-JJF-LPS, Document 67, filed Dec. 7, 2009, District of Delaware, United States District Court (17 pages).
Declaration of Michael A. Pearson, Jr. in Support of Braun's Response to Terumo's Counter-Statement in Response to Braun's Motion for Partial Summary Judgment on Terumo's Anticipation and Obviousness Invalidity Defenses and Counterclaims for Certain Claims of the '613 Patent, including Appendixes 15-22; Case No. 09 CV 00347-JJF-LPS, Document 252, filed Aug. 17, 2010; District of Delaware, United States District Court; Redacted—Public Version (82 pages).
Braun's Response to Terumo's Counter-Statements in Response to Braun's Motion for Partial Summary Judgment on Terumo's Anticipation and Obviousness Invalidity Defenses and Counterclaims for Certain Claims of the '613 Patent; Case No. 09 CV 00347-JJF-LPS, Document 251, filed Aug. 17, 2010, District of Delaware, United States District Court; Redacted—Public Version (15 pages).
Declaration of Douglas E. McCann in Support of Terumo's Counter-Statements of Genuine Issues of Material Fact in Response to Braun's Motions for Summary Judgment; Case No. 09 CV 00347-JJF-LPS, Document 234, filed Jul. 29, 2010, District of Delaware, United States District Court; Redacted (22 pages).
Declaration of Dr. John C. Kulli in Support of Terumo's Counter-Statements of Genuine Issues of Material Fact in Response to Braun's Motions for Summary Judgment; Case No. 09 CV 00347-JJF-LPS, Document 233, filed Jul. 29, 2010, District of Delaware, United States District Court; Redacted (75 pages).
Terumo's Counter-Statement of Genuine Issues of Material Fact in Response to Braun's Motion for Partial Summary Judgment on Terumo's Anticipation and Obviousness Invalidity Defenses and Counterclaims for Certain Claims of the '613 Patent; Case No. 09 CV 00347-JJF-LPS, Document 232, filed Jul. 29, 2010, District of Delaware, United States District Court; Redacted (24 pages).
Declaration of Michael A. Pearson, Jr. in Support of Braun's Motion for Partial Summary Judgment on Terumo's Anticipation and Obviousness Invalidity Defenses and Counterclaims for Certain Claims of the '613 Patent; Case No. 09 CV 00347-JJF-LPS, dated Jun. 25, 2010, District of Delaware, United States District Court; Redacted—Public Version (161 pages).
Braun's Opening Brief in Support of its Motion for Partial Summary Judgment on Terumo's Anticipation and Obviousness Invalidity Defenses and Counterclaims for Certain Claims of the '613 Patent; Case No. 09 347 JJF-LPS, dated Jun. 25, 2010, redacted version Jul. 2, 2010, District of Delaware, United States District Court; Redacted—Public Version (22 pages).
Braun's Motion for Partial Summary Judgment on Terumo's Anticipation and Obviousness Invalidity Defenses and Counterclaims for Certain Claims of the '613 Patent; Case No. 09 CV 00347-JJF-LPS, Document 200, Filed Jun. 25, 2010, District of Delaware, United States District Court (2 pages).
Opening Expert Report of Dr. John C. Kulli Regarding Certain Claims of U.S. Pat. No. 7,264,613, including Appendixes A-J; *B. Braun Melsungen AG & B. Braun Medical Inc.* v. *Terumo Medical Corporation & Terumo Corporation*, dated Apr. 9, 2010 (874 pages).
Terumo Medical Corporation & Terumo Corporation's First Supplemental Responses to B. Braun Melsungen AG & B. Braun Medical Inc.'s First Set of Interrogatories (No. 3), with Attachment A and Appendixes 2-11; Case No. 09-347-JJF, dated Sep. 22, 2009, District of Delaware, United States District Court (1506 pages).
Terumo Medical Corporation & Terumo Corporation's Supplemental Answers to B. Braun Melsungen AG & B. Braun Medical Inc.'s First Set of Interrogatories (Nos. 1-6); Case No. 09 347 JJF, dated Dec. 30, 2009, District of Delaware, United States District Court; Redacted (36 pages).
Terumo Medical Corporation & Terumo Corporation's Third Supplemental Answers to B. Braun Melsungen AG & B. Braun Medical Inc.'s First Set of Interrogatories (Nos. 2 and 3); Case No. 09-347-JJF, dated Feb. 26, 2010, District of Delaware, United States District Court; Redacted (23 pages).
Terumo Medical Corporation & Terumo Corporation's Fourth Supplemental Answers to B. Braun Melsungen AG & B. Braun Medical Inc.'s First Set of Interrogatories (No. 3), Case No. 09 347 JJF-LPS, dated Mar. 11, 2010, District of Delaware, United States District Court; Redacted (22 pages).
Decision on Opposition by Terumo Corporation; In the Court of the Commissioner of Patents for the Australian Patent Office; Patent Application No. 2006200679 in the name of B. Braun Melsungen AG; *Terumo Corporation v. B. Braun Melsungen AG* [2011] APO 71 dated Sep. 16, 2011 (17 pages).
Hoffer, Erik K. et al., "Peripherally Inserted Central Catheters with Distal versus Proximal Valves: Prospective Randomized Trial", Journal of Vascular and Interventional Radiology, Oct. 2001, pp. 1173-1177, vol. 12 No. 10 (5 pages).
Evidence in Support—Smith Declaration—Annex MS-K. Aug. 27, 2014. (23 sheets).
Evidence in Support—Smith Declaration—Annex MS-L. Aug. 27, 2014. (18 sheets).
Evidence in Support—Smith Declaration—Annex MS-M. Aug. 27, 2014. (31 sheets).
Evidence in Support—Smith Declaration—Annex MS-N. Aug. 27, 2014. (5 sheets).
Evidence in Support—Smith Declaration—Annex MS-O. Aug. 27, 2014. (32 sheets).
Evidence in Support—Smith Declaration—Annex MS-P. Aug. 27, 2014. (48 sheets).
Evidence in Support—Smith Declaration—Annex MS-Q. Aug. 27, 2014. (143 sheets).

(56) References Cited

OTHER PUBLICATIONS

US Priority Document U.S. Appl. No. 09/590,600. Printed Aug. 4, 2001. (144 sheets).
Evidence in Answer—Esnouf Declaration of Patent Application 2013248192. Feb. 6, 2015. (65 sheets).
Evidence in Answer—Haindl Declaration of Patent Application 2013248192. Feb. 16, 2015. (57 sheets).
Evidence in Answer—Mickan Declaration of Patent Application 2013248192. Feb. 13, 2015. (108 sheets).
Evidence in Reply—Chrysiliou Third Declaration. AU Patent Application No. 2013248192. Apr. 24, 2015. (47 sheets).
Evidence in Reply—Chrysiliou Third Declaration—Annex KC-65. AU Patent Application No. 2013248192. Apr. 24, 2015. (55 sheets).
Evidence in Reply—Chrysiliou Third Declaration—Annex KC-69. AU Patent Application No. 2013248192. Apr. 24, 2015. (57 sheets).
Evidence in Reply—Chrysiliou Third Declaration—Annex KC-74. AU Patent Application No. 2013248192. Apr. 24, 2015. (59 sheets).
Evidence in Reply—Chrysiliou Third Declaration—Annex KC-75. AU Patent Application No. 2013248192. Apr. 24, 2015. (58 sheets).
Evidence in Reply—Chrysiliou Third Declaration—Annex KC-79. AU Patent Application No. 2013248192. Apr. 24, 2015. (46 sheets).
Evidence in Reply—Chrysiliou Third Declaration—Annex KC-85. AU Patent Application No. 2013248192. Apr. 24, 2015. (59 sheets).
Letter to IPA Filing Third Declaration of Chrysiliou. Apr. 24, 2015. (1 sheet).
Evidence in Reply—Chrysiliou Third Declaration—Annex KC-35. AU Patent Application No. 2013248192. Nov. 20, 2014. (111 sheets).
Evidence in Reply—Chrysiliou Third Declaration—Annex KC-46. AU Patent Application No. 2013248192. Nov. 20, 2014. (92 sheets).
Evidence in Reply—Chrysiliou Third Declaration—Annex KC-48. AU Patent Application No. 2013248192. Nov. 20, 2014. (161 sheets).
Evidence in Reply—Chrysiliou Third Declaration—Annex KC-49. AU Patent Application No. 2013248192. Nov. 20, 2014. (4 sheets).
Evidence in Reply—Chrysiliou Third Declaration—Annex KC-50. AU Patent Application No. 2013248192. Nov. 20, 2014. (147 sheets).
Evidence in Reply—Chrysiliou Third Declaration—Annex KC-51. Au Patent Application No. 2013248192. Nov. 20, 2014. (31 sheets).
Evidence in Reply—Chrysiliou Third Declaration—Annex KC-52. AU Patent Application No. 2013248192. Nov. 20, 2014. (42 sheets).
Evidence in Reply—Chrysiliou Third Declaration—Annex KC-58. AU Patent Application No. 2013248192. Nov. 20, 2014. (44 sheets).
Evidence in Support—Chrysiliou Second Declaration. AU Patent Application No. 2013248192. Nov. 20, 2014. (6 sheets).
Evidence in Support—Leskowich Declaration. Sep. 2, 2014. (46 sheets).
Evidence in Support—Leskowich Declaration—Annex B. Sep. 2, 2014. (41 sheets).
Letter to IPA Filing Evidence in Support. Nov. 20, 2014. AU Patent Application No. 2013248192. (1 Sheet).
Introcan Safety I.V. Catheter. B. Braun Advertisement—New Products Page. www.bbraunusa.com/news_prod.htm. Printed Mar. 3, 2000 (2 sheets).
Safety IV Catheter. Hospital Network Advertisement—New Products Page. www.hospitalnetwork.com/doc/safety-iv-catheter-0001. Printed Dec. 15, 1999 (1 sheet).
I.V. Catheter Engages Needletip Shield. MED Device Online Advertisement. www.meddeviceonline.com/doc/iv-catheter-engages-needletip . . . Printed Dec. 23, 1999 (1 sheet).
510(k) Summary of Safety and Effectiveness in Accordance with SMDA '90. Regulatory Affairs Notification Printed Aug. 4, 1998. (5 sheets).
US Priority Document U.S. Appl. No. 08/915,148. Printed Jul. 6, 1998. (30 sheets).
US Priority Document U.S. Appl. No. 09/097,170. Printed Jul. 13, 1998. (46 sheets).
Evidence in Answer—Mickan Declaration. Dec. 19, 2014. (2 sheets).
Evidence in Answer—Annexure SPM-1. Dec. 19, 2014. (107 sheets).
Evidence in Answer—Annexure SPM-2. Dec. 19, 2014. (73 sheets).
Evidence in Answer—Esnouf Declaration. Dec. 18, 2014. (65 sheets).
Evidence in Answer—Haindl Declaration. Dec. 17, 2014. (66 sheets).
Letter to IP Australia—Filing Evidence in Answer. Dec. 19, 2014. (1 sheet).
Evidence in Reply—Chrysiliou Fifth Declaration. Feb. 23, 2105. (27 sheets).
Evidence in Reply—Chrysiliou Fifth Declaration—Annex KC-57. Feb. 23, 2105. (48 sheets).
Evidence in Reply—Chrysiliou Fifth Declaration—Annex KC-59. Feb. 23, 2105. (5 sheets).
Evidence in Reply—Chrysiliou Fifth Declaration—Annex KC-61. Feb. 23, 2105. (25 sheets).
Evidence in Reply—Chrysiliou Fifth Declaration—Annex KC-64. Feb. 23, 2105. (4 sheets).
Evidence in Reply—Chrysiliou Fifth Declaration—Annex KC-66. Feb. 23, 2105. (53 sheets).
Evidence in Reply—Chrysiliou Fifth Declaration—Annex KC-69. Feb. 23, 2105. (58 sheets).
Evidence in Reply—Chrysiliou Fifth Declaration—Annex KC-70. Feb. 23, 2105. (61 sheets).
Evidence in Reply—Chrysiliou Fifth Declaration—Annex KC-75. Feb. 23, 2105. (41 sheets).
Evidence in Reply—Chrysiliou Fifth Declaration—Annex KC-79. Feb. 23, 2105. (38 sheets).
Evidence in Reply—Chrysiliou Fifth Declaration—Annex KC-83. Feb. 23, 2105. (37 sheets).
Letter to IP Australia—Filing Evidence in Reply. Feb. 23, 2015. (1 sheet).
Application for Extension of Time to File Evidence. Chrysiliou. Patent Application No. 2013202166. Aug. 28, 2014. (3 sheets).
Letter from Chysiliou IP to IP Australia. Extension of Time Request. AU Patent Application No. 2013202166. Aug. 29, 2014. (1 sheet).
Letter from IPA to Chrysiliou IP Acknowledge Extension of Time. AU Patent Application No. 2013202166. Aug. 29, 2014. (1 sheet).
Letter from IPA to Chrysiliou IP Acknowledge Part Evidence in Support. AU Patent Application No. 2013202166. Aug. 29, 2014. (1 sheet).
Evidence in Support—Bennett Declaration. Aug. 27, 2014. (21 sheets).
Evidence in Support—Butler Declaration. Aug. 19, 2014. (6 sheets).
Evidence in Support—Chrysiliou First Declaration. Aug. 28, 2014. (68 sheets).
Evidence in Support—Chrysiliou First Declaration, Annex KC-4 Aug. 28, 2014. (37 sheets).
Evidence in Support—Chrysiliou First Declaration, Annex KC-16 Aug. 28, 2014. (31 sheets).
Evidence in Support—Chrysiliou First Declaration, Annex KC-28 Aug. 28, 2014. (14 sheets).
Evidence in Support—Chrysiliou Fourth Declaration. Aug. 28, 2014. (43 sheets).
Evidence in Support—Chrysiliou Second Declaration. Aug. 28, 2014. (98 sheets).
Evidence in Support—Chrysiliou Second Declaration—Annex KC-44. Aug. 28, 2014. (61 sheets).
Evidence in Support—Chrysiliou Third Declaration. Aug. 28, 2014. (81 sheets).
Evidence in Support—Chrysiliou Third Declaration—Annex KC-49. Aug. 28, 2014. (24 sheets).
Evidence in Support —Chrysiliou Third Declaration—Annex KC-52. Aug. 28, 2014. (88 sheets).
Evidence in Support—Smith Declaration. Aug. 27, 2014. (3 sheets).
Evidence in Support—Smith Declaration—Annex MS-A. Aug. 27, 2014. (4 sheets).
Evidence in Support—Smith Declaration—Annex MS-B. Aug. 27, 2014. (35 sheets).
Evidence in Support—Smith Declaration—Annex MS-C. Aug. 27, 2014. (3 sheets).
Evidence in Support—Smith Declaration—Annex MS-D. Aug. 27, 2014. (53 sheets).
Evidence in Support—Smith Declaration—Annex MS-E. Aug. 27, 2014. (4 sheets).

(56) References Cited

OTHER PUBLICATIONS

Evidence in Support—Smith Declaration—Annex MS-F. Aug. 27, 2014. (21 sheets).
Evidence in Support—Smith Declaration—Annex MS-G. Aug. 27, 2014. (31 sheets).
Evidence in Support—Smith Declaration—Annex MS-H. Aug. 27, 2014. (4 sheets).
Evidence in Support—Smith Declaration—Annex MS-I. Aug. 27, 2014. (23 sheets).
Evidence in Support—Smith Declaration—Annex MS-J. Aug. 27, 2014. (5 sheets).

* cited by examiner

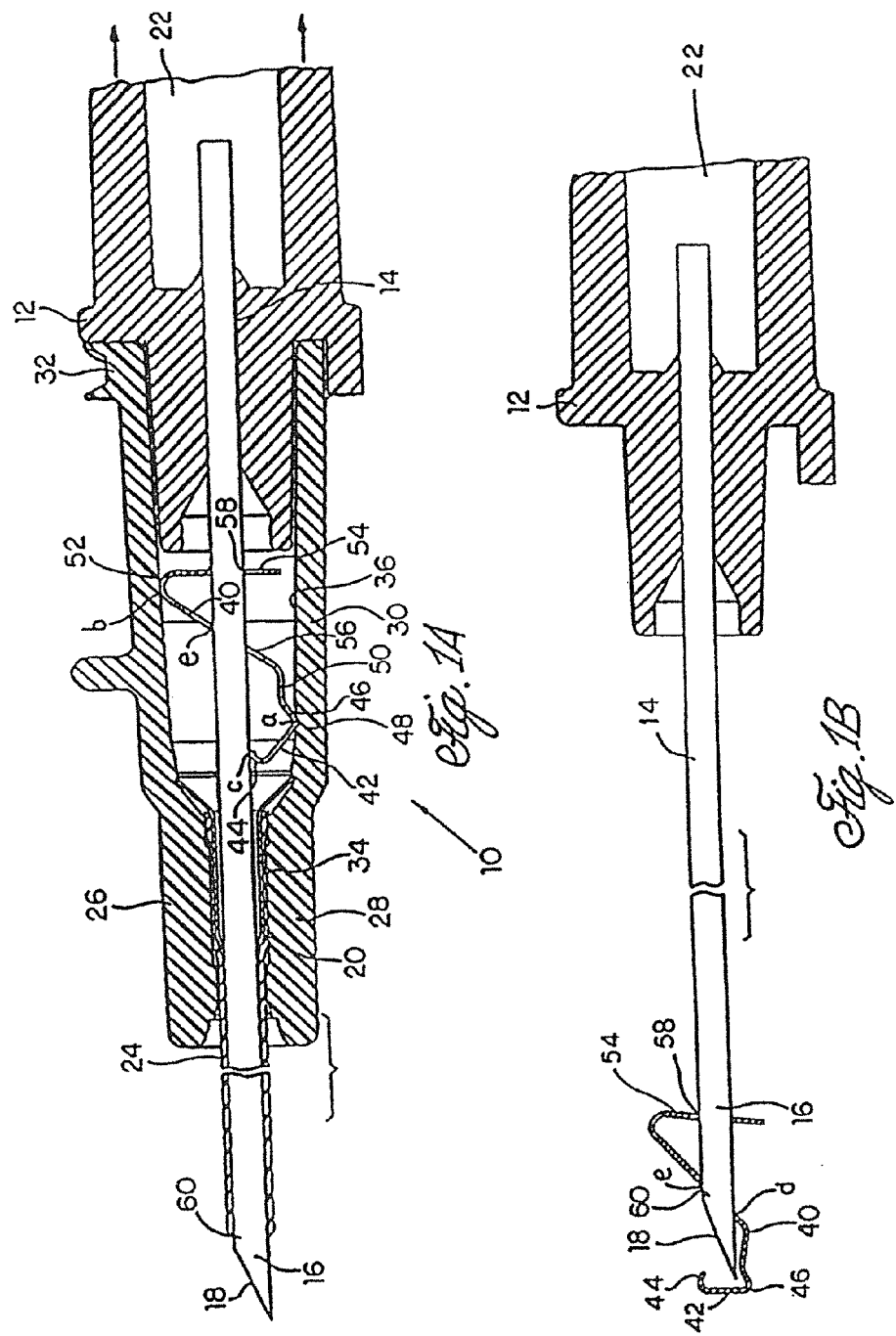

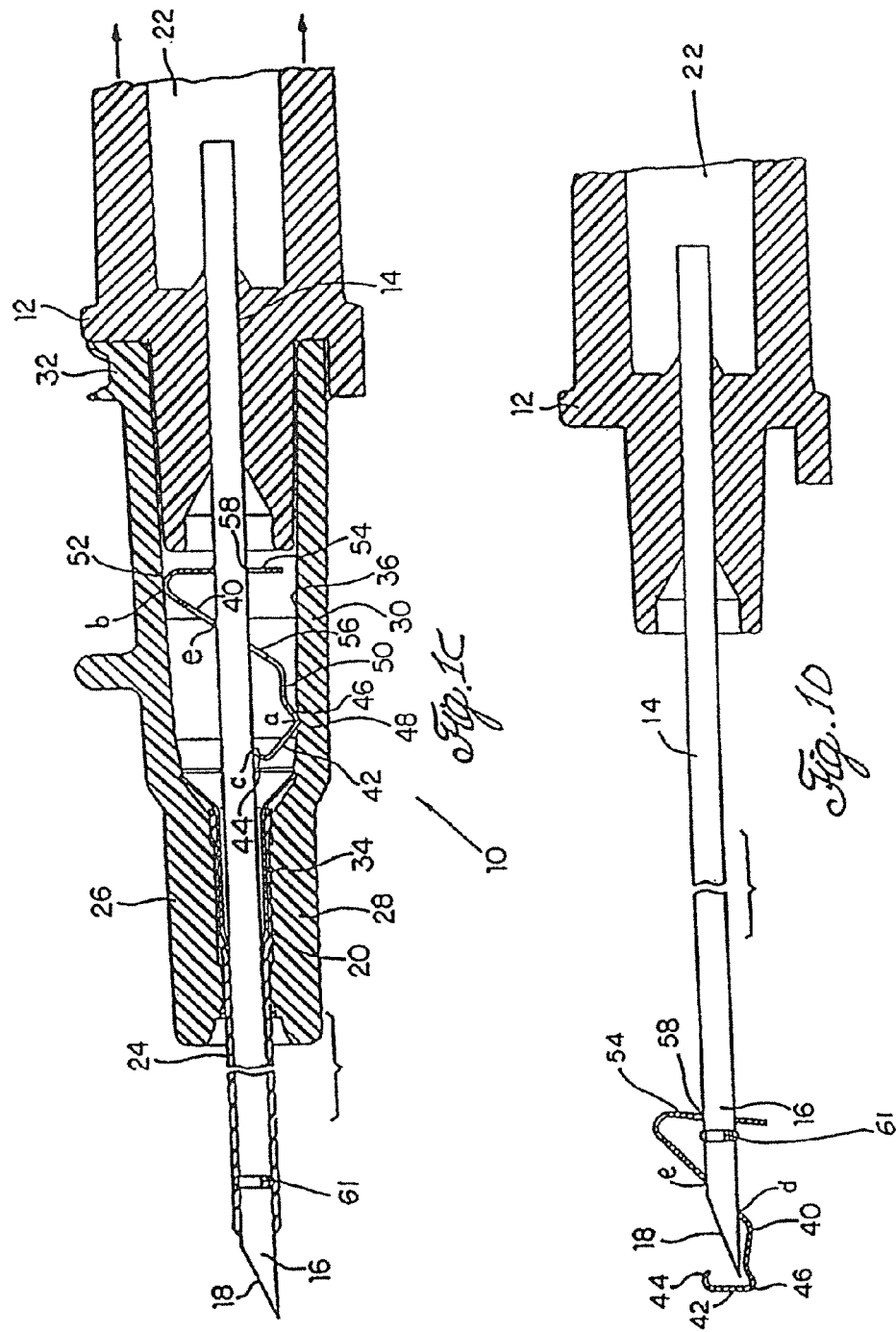

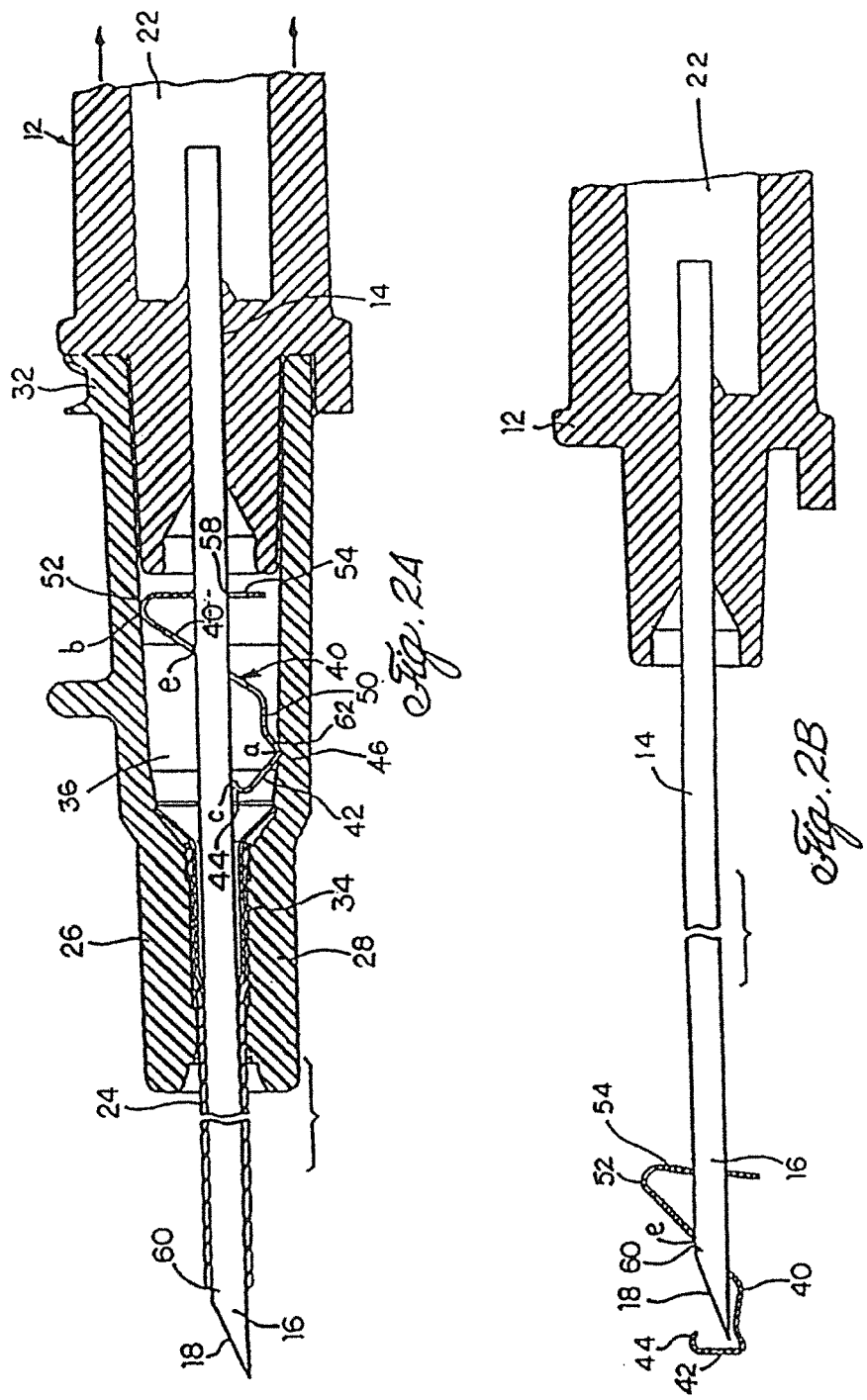

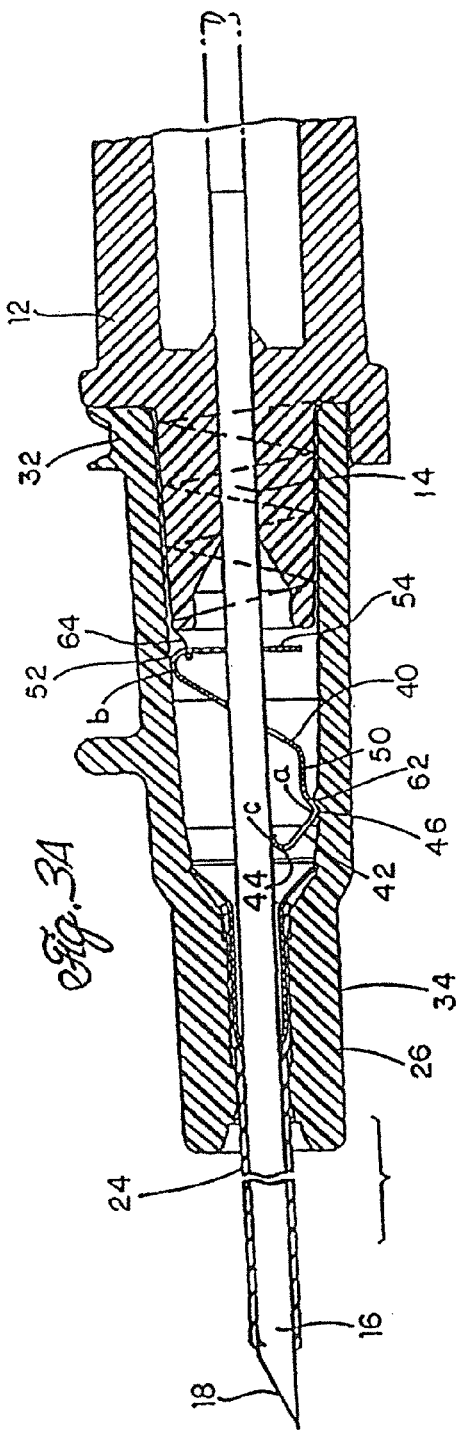
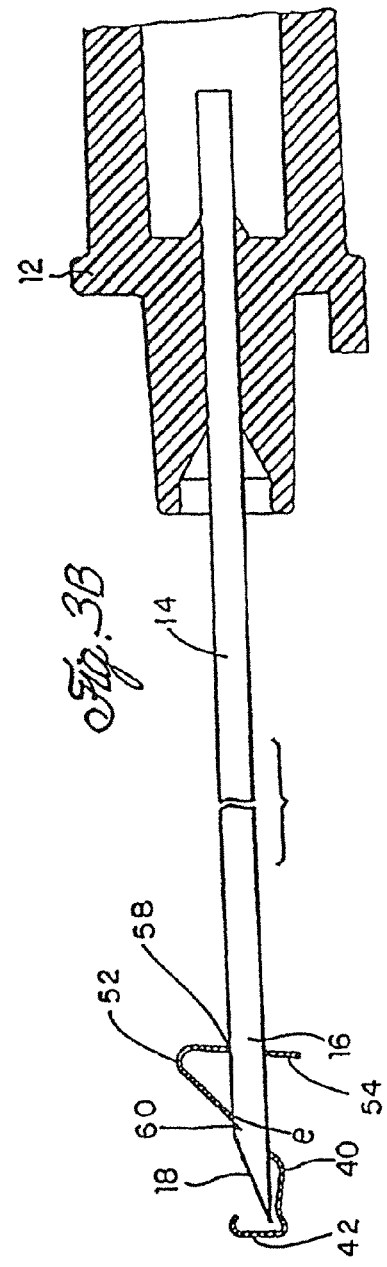

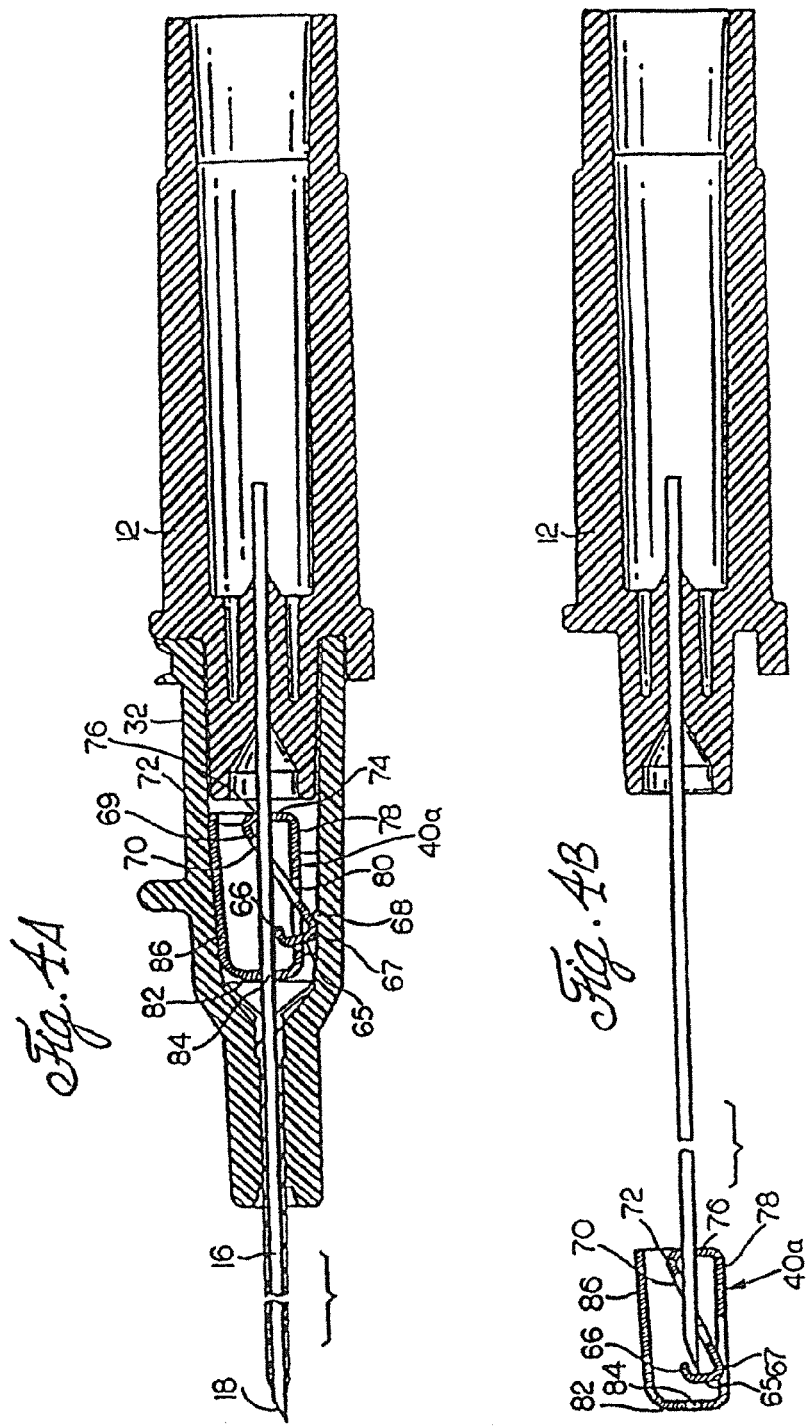

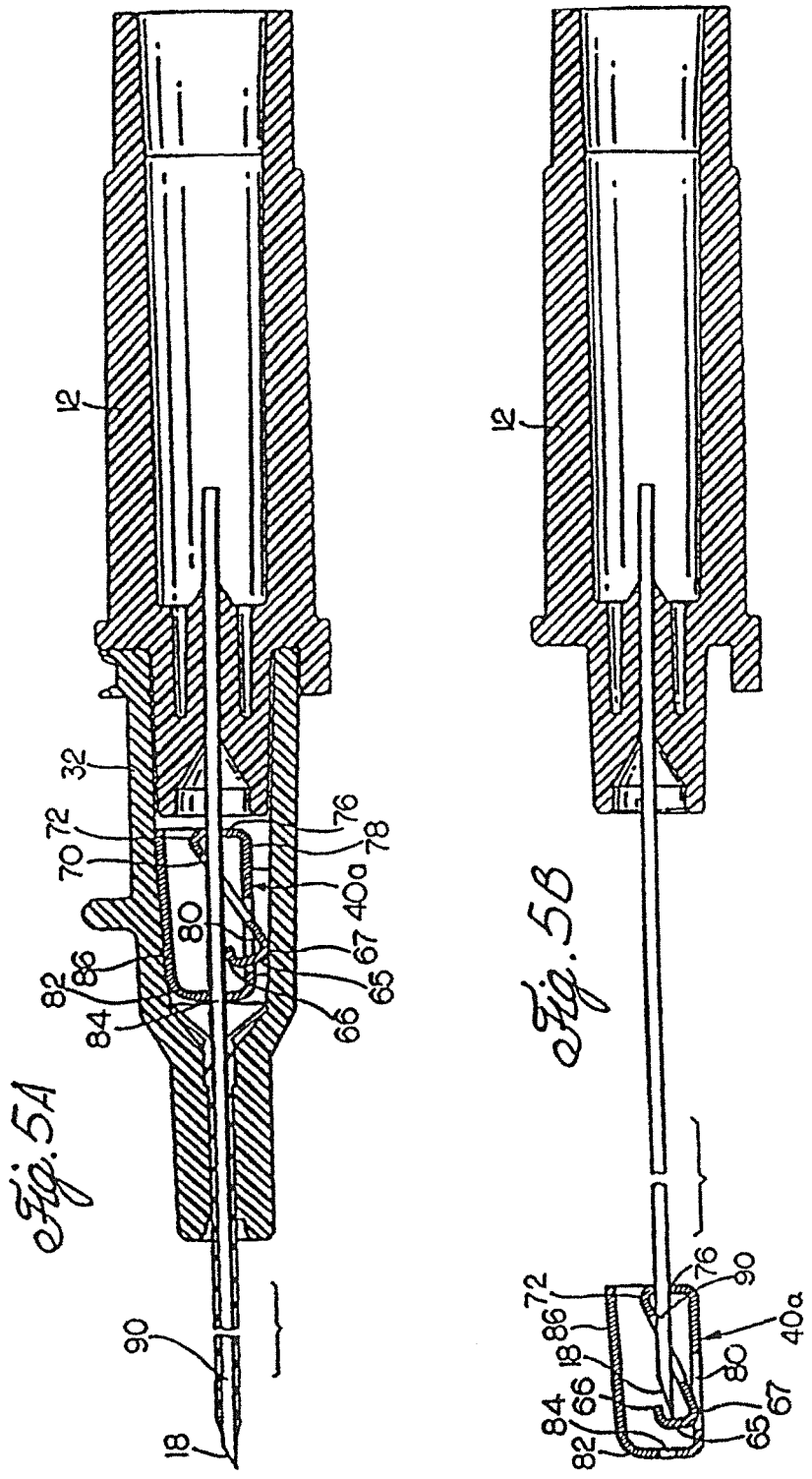

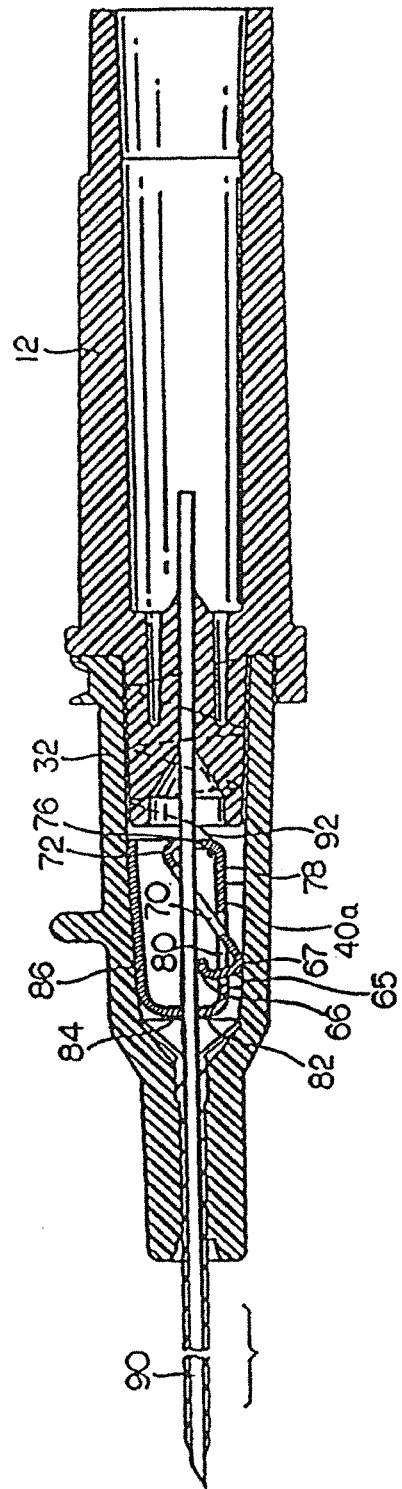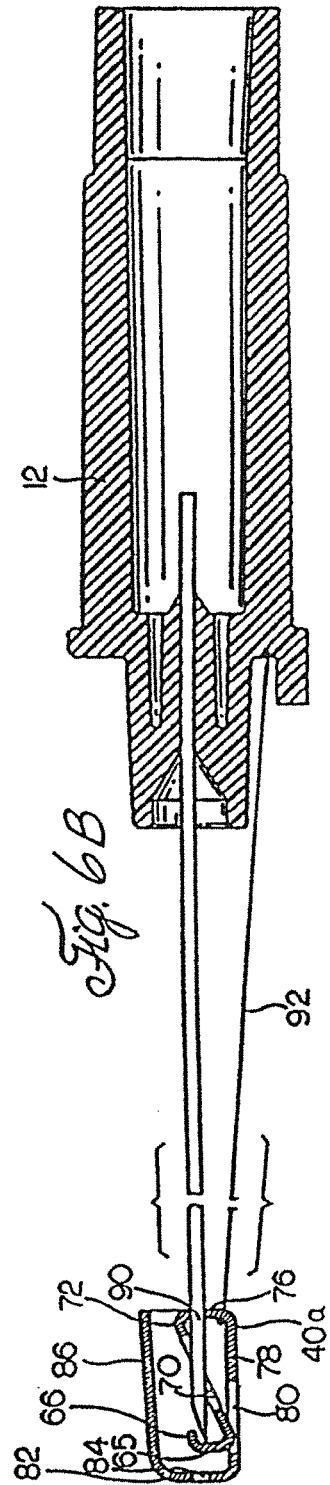

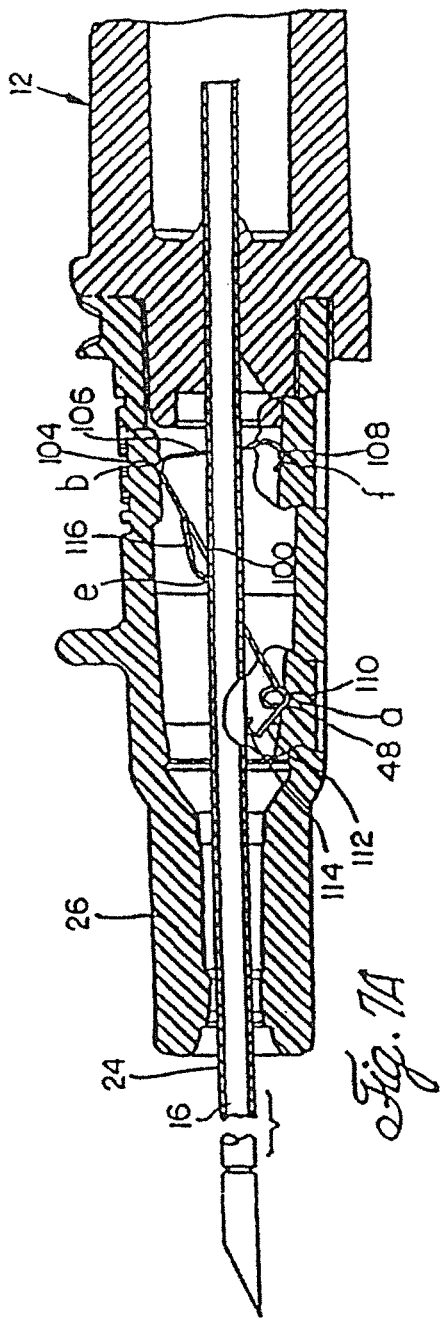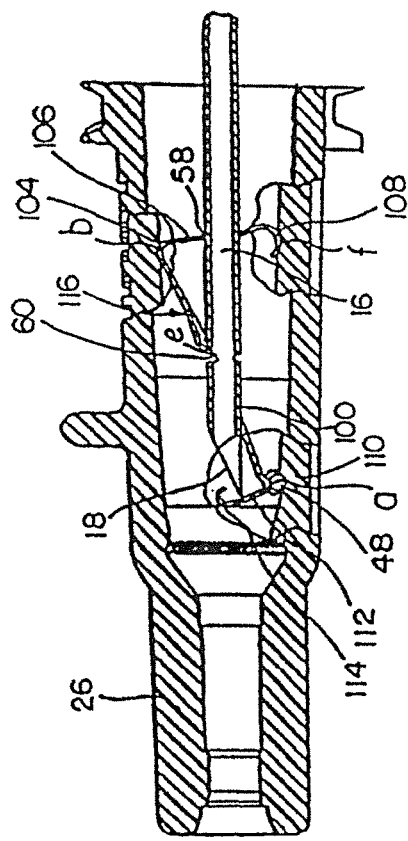
Fig. 7A
Fig. 7B

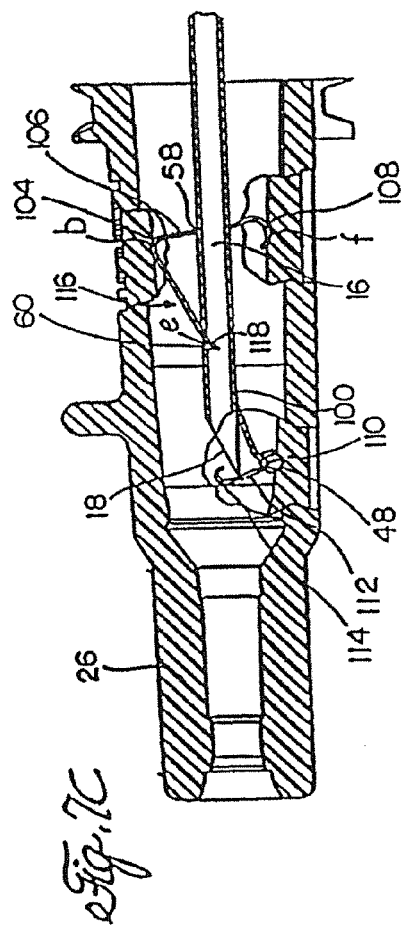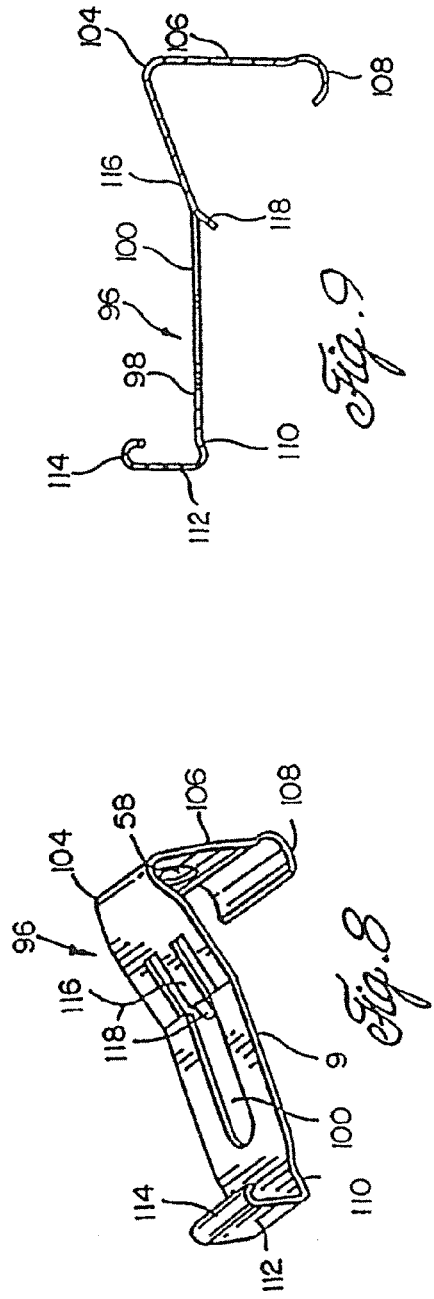

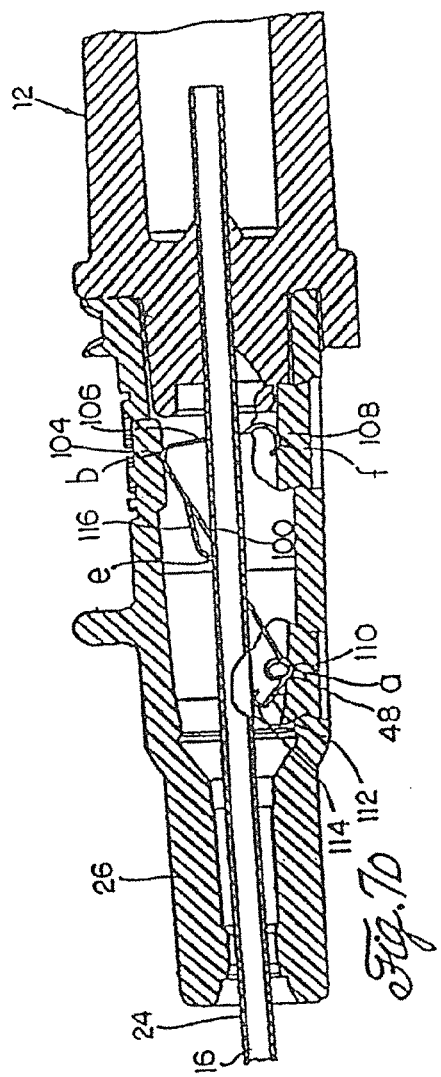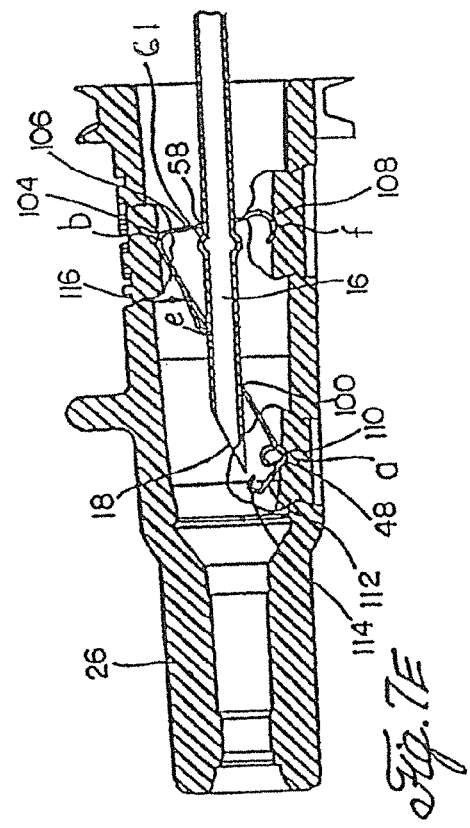

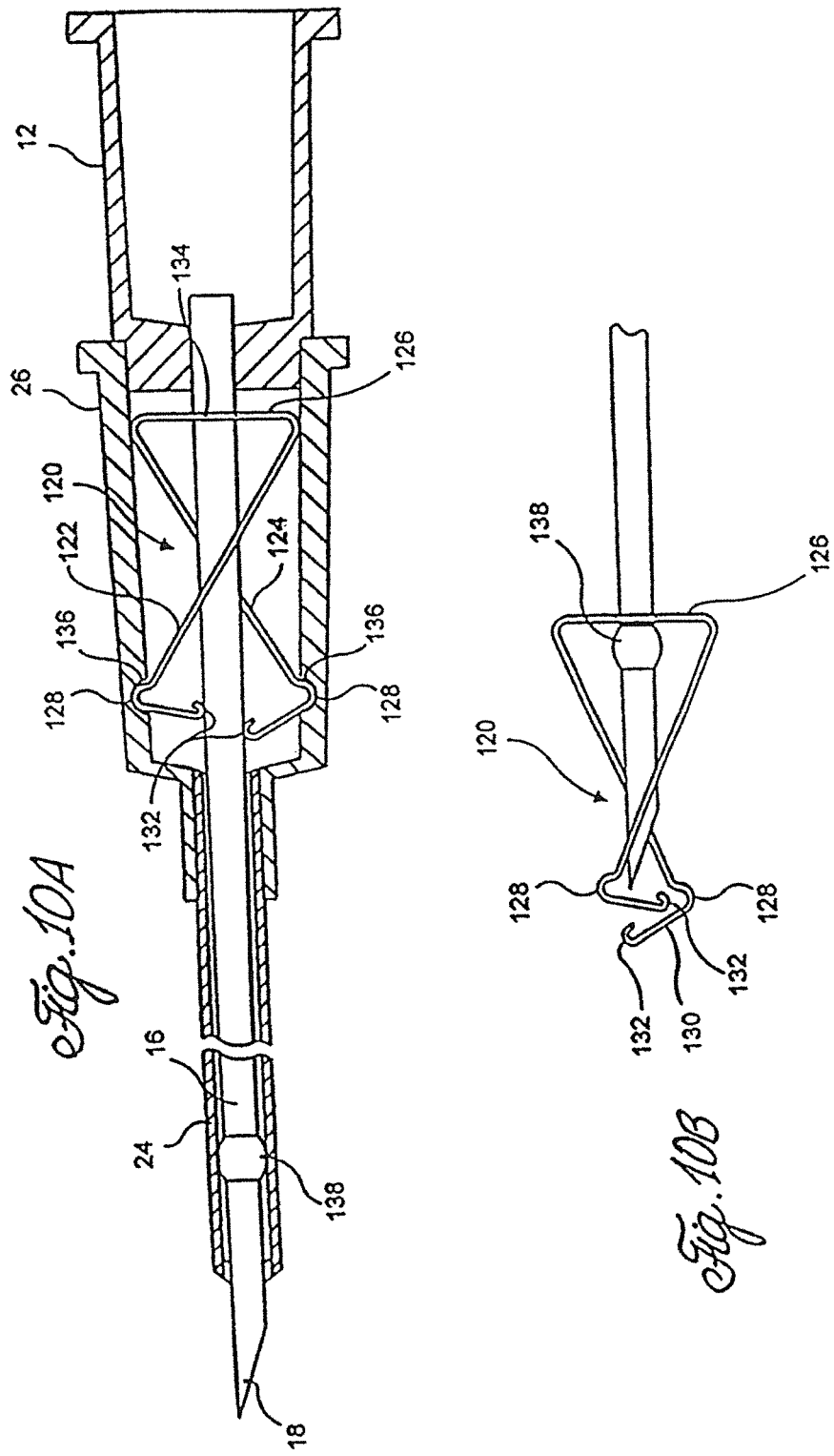

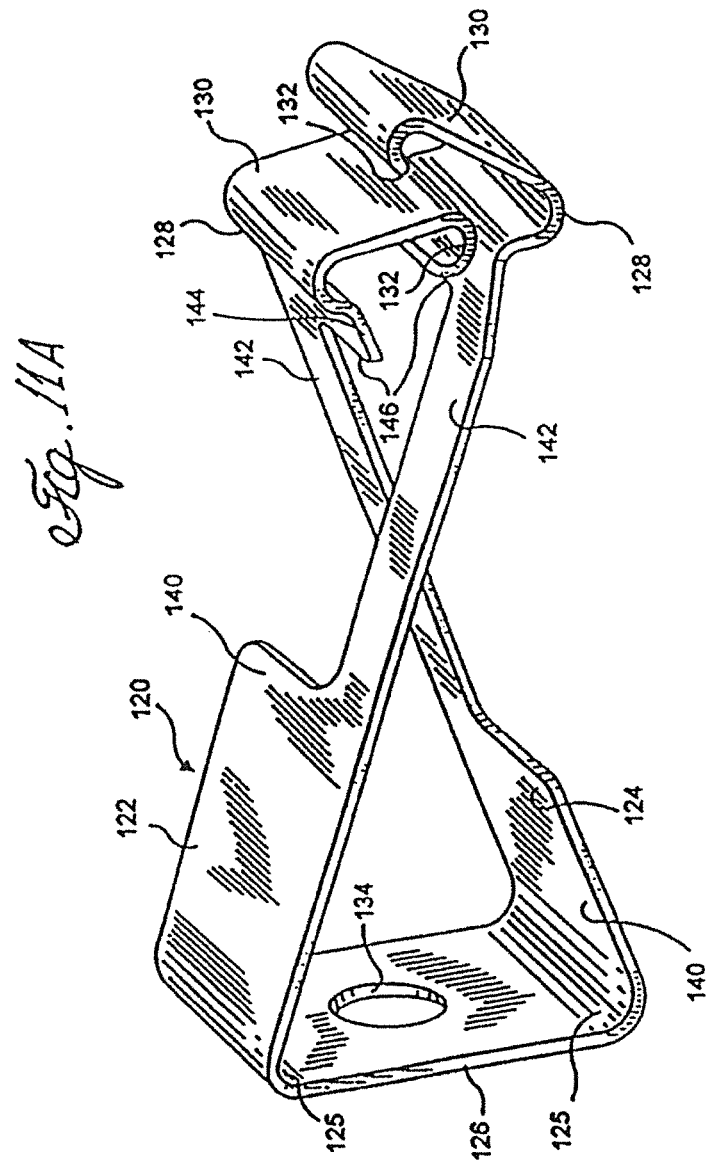

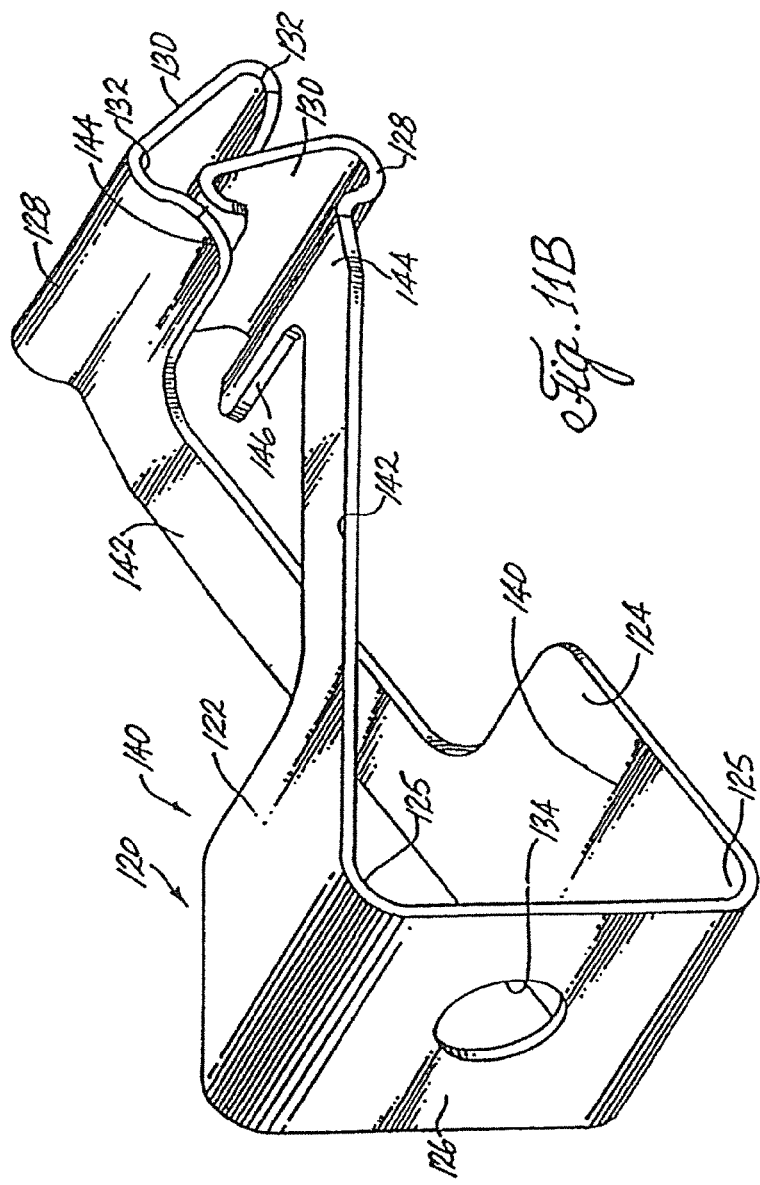

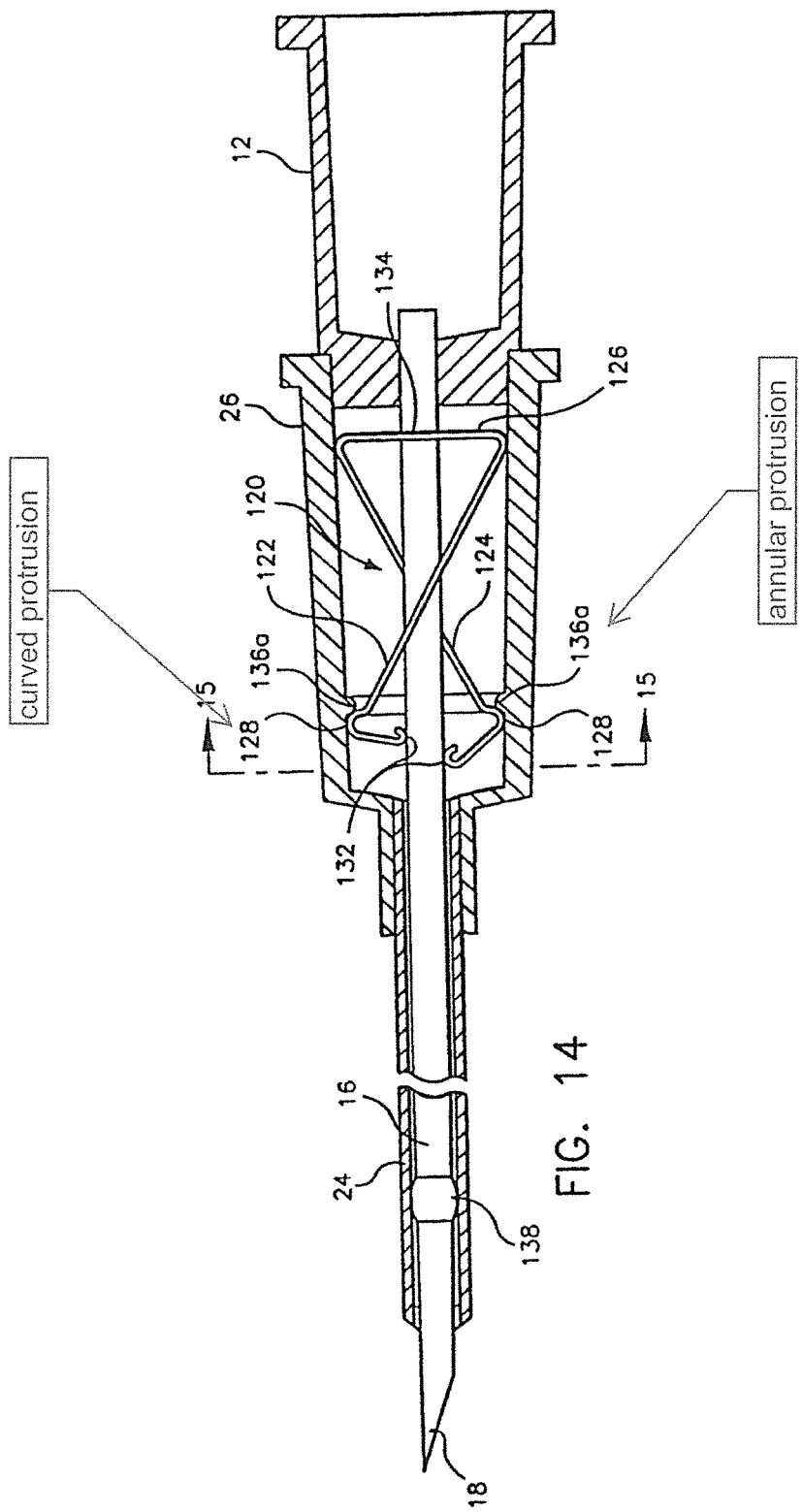

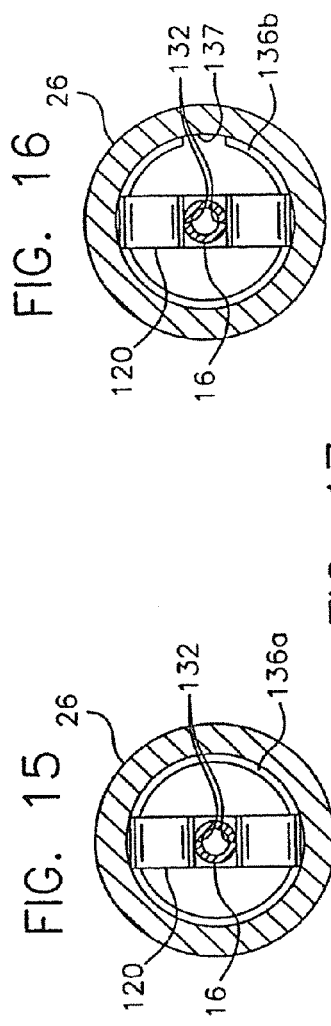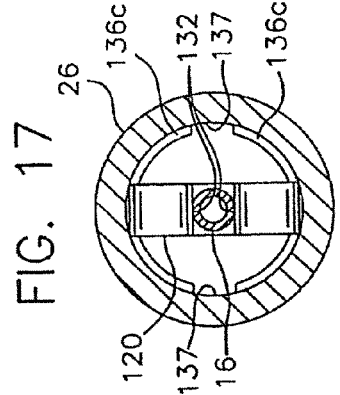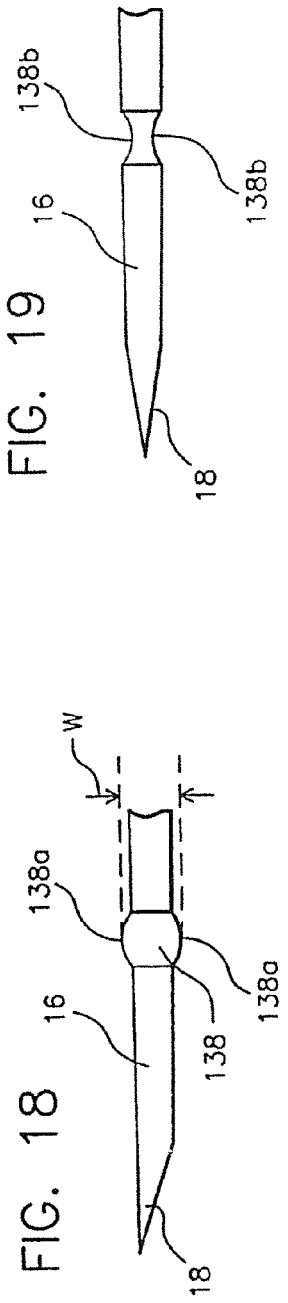

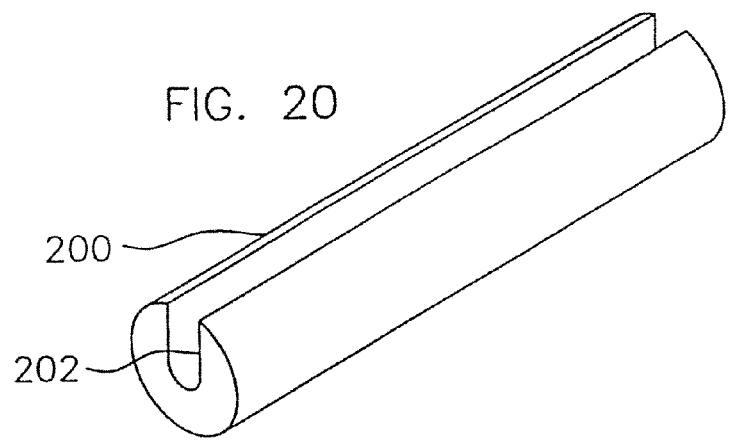
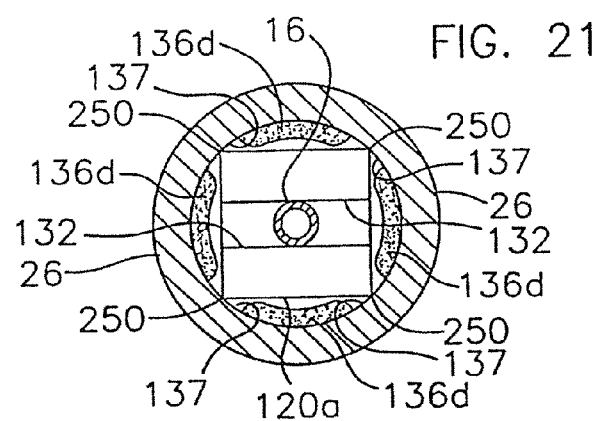
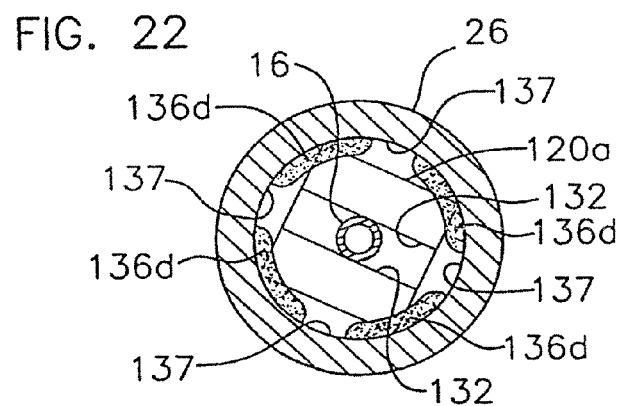

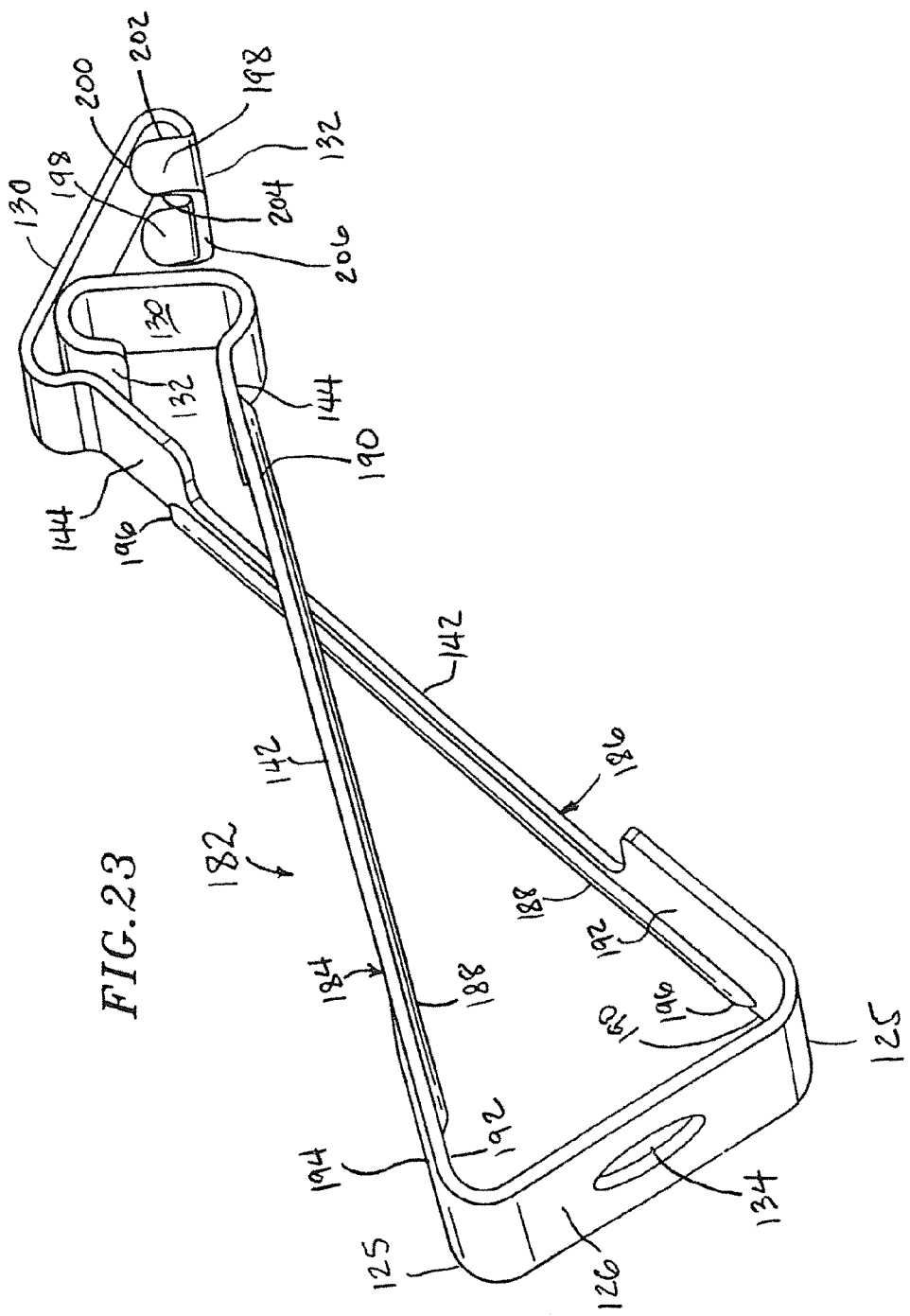

SPRING CLIP SAFETY IV CATHETER

FIELD OF THE INVENTION

This invention relates generally to intravenous (IV) catheters, and, in particular, to a safety IV catheter in which the needle tip is automatically covered after needle withdrawal to prevent the healthcare worker from making accidental contact with the needle tip.

BACKGROUND OF THE INVENTION

IV catheters are primarily used to administer fluids, sometimes containing medications, directly into a patient's vascular system. The catheter is inserted into a patient's vein by a healthcare worker by using a handheld placement device that includes a sharp tip needle. The needle is positioned in the interior hollow portion of the catheter with its tip extended slightly beyond the edge of the catheter. The end of the apparatus opposite the needle tip is made up of the needle connected to a needle hub which is capable of being held by the healthcare worker during the insertion procedure.

The insertion procedure contains four basic steps: (1) the healthcare worker inserts the needle and catheter together into the patient's vein; (2) after insertion into the vein with the needle point, the catheter is forwarded into the vein of the patient by the healthcare worker pushing the catheter with his or her finger; (3) the healthcare worker withdraws the needle by grasping the hub end (opposite the point end) while at the same time applying pressure to the patient's skin at the insertion site with his or her free hand; and (4) the healthcare worker then tapes the now inserted catheter to the patient's skin and connects the exposed end of the catheter (the catheter hub) to the source of the fluid to be administered into the patient's vein.

The problem is that, immediately after the withdrawal of the needle from the patient's vein, the healthcare worker, who is at this time involved in at least two urgent procedures, must place the exposed needle tip at a nearby location and address the tasks required to accomplish the needle withdrawal. It is at this juncture that the exposed needle tip creates a danger of an accidental needle stick occurring, which, under the circumstances, leaves the healthcare worker vulnerable to the transmission of various dangerous blood-borne pathogens, including AIDS and hepatitis.

This danger to the healthcare worker from accidental needle sticks has caused an impetus for the development of a safer IV catheter in which the occurrence of such accidental needle sticks is prevented. Safety catheters that have been developed to achieve this result are disclosed, for example, in Lemieux Reissue Pat. No. Re. 34,416, Crawford U.S. Pat. No. 5,558,651, McLees U.S. Pat. No. 5,135,504, Gaba U.S. Pat. No. 5,697,907, and Dombrowski U.S. Pat. No. 4,978,344. Kulli U.S. Pat. No. 4,929,241 and Chamuel U.S. Pat. No. 5,053,107 disclose a protective needle guard for use with a hypodermic needle.

The prior art safety catheters all exhibit one or more drawbacks that have thus far limited their usefulness and full acceptance by healthcare workers. For example, in the safety catheter disclosed in the Lemieux patent, the force required to engage the needle slot within the guard flange is relatively great and would interfere with the removal of the needle. Reducing this force to a more acceptable level would create the possibility of the needle guard remaining in the catheter hub after the needle is removed from the catheter. As a result, the safety catheter disclosed in the Lemieux patent would not consistently function in a reliable manner.

Similarly, the user of the safety catheter disclosed in the Dombrowski patent would have to exert a considerable force to remove the protective cap from the catheter hub when the cap engages a needle. The safety catheter disclosed in the Dombrowski patent would also be relatively expensive to fabricate because of its inclusion of a flexible flange and a tether.

The McLees protective device requires an irksome extra pulling action or tug on the needle guard through a retention ring to remove the protected needle from the catheter hub. The McLees device also requires the assembly of two separate components and is thus relatively costly to manufacture. In addition, the needle in the McLees device includes a larger diameter portion near and at the needle tip. This feature of the McLees device would require that the remainder of the needle be of a lesser diameter which would have the adverse effect of slowing the blood flashback through the needle.

SUMMARY OF THE INVENTION

It is accordingly an object of the present invention to provide a safety IV catheter which reliably and automatically prevents accidental, inadvertent contact with the needle tip after use.

It is a further object of the invention to provide a safety catheter which provides reliable protection to the healthcare practitioner against needle sticks without requiring any change in the manner of use of the safety catheter by the practitioner.

It is another object of the present invention to provide a safety IV catheter of the type described which is relatively simple and inexpensive to manufacture.

It is yet a further object of the present invention to provide a safety catheter of the type described in which removal of the needle from the needle guard after use is prevented.

To these ends, the safety IV catheter of the invention includes a resilient spring clip needle guard that includes a distal or front end and a proximal or rear wall. The spring clip is inserted into the catheter hub and is urged by the needle shaft into contact with the inner walls of the catheter hub so that the needle guard is reliably retained therein. When the needle is withdrawn from the catheter, the force it had previously exerted on the needle guard is released, causing the needle guard to pivot within the catheter hub until it clamps onto the needle shaft. At this time, the distal end wall of the needle guard blocks the distal pointed end tip of the needle. In addition, the spring clip and protected needle onto which it is clamped can be readily and safely removed from the catheter hub. The needle may be provided with a slot or, alternatively, may be provided with a segment of increased width, such as a crimp, which cooperates with the needle guard to prevent the inadvertent removal of the needle from the needle guard after their removal from the catheter hub.

In another embodiment, an IV catheter apparatus is provided which comprises a tubular catheter having a proximal end and a distal end and a needle having a needle shaft and a tip, where the needle is received within the tubular catheter when in a ready position. A catheter hub is attached to the proximal end of the catheter, where the catheter hub has a hollow interior and an inner wall. The needle is movable between the ready position, in which the tip is outside of the catheter hub, and a retracted position, in which the tip is within the interior of the catheter hub. A unitary needle guard is positioned in the interior of the catheter hub and includes a resilient portion engaged by the needle shaft when the needle is in its ready position. A section of the resilient portion of the needle guard is urged by the needle shaft into contact with an interior wall of the catheter hub when the needle is in its ready position. An inwardly extending annular protrusion is formed on the interior wall of the catheter hub for engaging a segment of the needle guard for retaining the needle guard in the catheter hub during the movement of the needle between its ready position and its retracted position. The needle guard includes a distal wall extending from the resilient portion and spaced from the needle tip when the needle is in its ready position and movable within the interior of the catheter hub to a blocking position distal of the needle tip when the needle is in its retracted position in which the needle shaft no longer exerts a force on the resilient portion of the needle guard, such that contact between the segment of the needle guard and the catheter hub is released.

In another embodiment of the spring clip safety catheter of the invention, a retaining groove or bump is formed in the inner wall of the catheter hub, which, in the ready position, engages a lower arm of the spring clip to aid in the retention of the spring clip in the catheter hub.

In yet a further embodiment of the spring clip safety catheter of the invention, a slot is formed in the needle. After the spring clip has pivoted to its retracted position and the needle is clamped by the spring clip, further movement of the needle in the proximal direction will cause the rear or proximal arm of the spring clip to seat in the slot, thereby to more securely clamp the needle shaft to the spring clip.

In a further embodiment of the spring clip catheter guard of the invention, a tether is connected to the needle hub and the spring clip guard to prevent the spring clip guard from being pulled off the protected needle without requiring an excessive clamping force therebetween.

In yet a further embodiment of the invention, the spring clip needle guard is in the form of resilient intersecting arms, each terminating at a distal guard wall. When the needle is in the ready position, it passes through the guard and urges the resilient arms away from each other and against the inner wall of the catheter hub. When the needle is retracted past the guard walls, the resilient arms spring to the safety position in which both of the guard walls are positioned distally from the needle tip, thereby to form a barrier that prevents inadvertent contact with the needle tip.

To the accomplishment of the above, and to such further objects as may hereinabove appear, the present invention relates to a safety IV catheter as described with respect to presently preferred embodiments in the following specification, as considered with the accompanying drawings.

BRIEF DESCRIPTION OF THE DRAWINGS

FIGS. 1A and 1B are semi-schematic views in partial cross-section of a safety IV catheter in accordance with a first embodiment of the invention in the ready and retracted positions, respectively;

FIGS. 1C and 1D are semi-schematic views similar to FIGS. 1A and 1B of a possible variation to the embodiment illustrated therein;

FIGS. 2A and 2B are semi-schematic views in partial cross-section of a safety IV catheter in accordance with a second embodiment of the invention in the ready and retracted positions, respectively;

FIGS. 3A and 3B are semi-schematic views in partial cross-section of a safety IV catheter in accordance with a third embodiment of the invention in the ready and retracted positions, respectively;

FIGS. 4A and 4B are semi-schematic views in partial cross-section of a safety IV catheter in accordance with a fourth embodiment of the invention in the ready and retracted positions, respectively;

FIGS. 5A and 5B are semi-schematic views in partial cross-section of a safety IV catheter in accordance with a fifth embodiment of the invention in the ready and retracted positions, respectively;

FIGS. 6A and 6B are semi-schematic views in partial cross-section of a safety IV catheter in accordance with a sixth embodiment of the invention in the ready and retracted positions, respectively;

FIGS. 7A, 7B and 7C are views in partial cross-section of a safety IV catheter in accordance with a further embodiment of the invention in the ready, engaged and retracted or protected positions, respectively;

FIGS. 7D and 7E are semi-schematic views similar to FIGS. 7A and 7b of a possible variation to the embodiment of the invention illustrated therein;

FIG. 8 is a semi-schematic perspective of the spring clip needle guard used in the embodiment of FIG. 7;

FIG. 9 is a semi-schematic cross-section of the spring clip needle guard of FIG. 8;

FIGS. 10A and 10B are semi-schematic views in partial cross-section of a safety IV catheter in accordance with still a further embodiment of the invention shown in the ready and protected positions, respectively;

FIGS. 11A and 11B are semi-schematic perspectives of the needle guard clip of the embodiment of FIG. 10;

FIG. 14 is a semi-schematic view in partial cross-section of a safety IV catheter in accordance with still a further embodiment of the invention, wherein an inwardly extending annular protrusion is provided to releasably retain the needle guard within the catheter hub;

FIG. 15 is a semi-schematic cross-sectional view taken along line 15 of FIG. 14, showing a continuous generally annular protrusion;

FIG. 16 is a semi-schematic cross-sectional view similar to that of FIG. 15, showing a generally annular protrusion having a small discontinuity formed therein;

FIG. 17 is a semi-schematic cross-sectional view similar to that of FIG. 15, showing a two-part annular protrusion;

FIG. 18 is a semi-schematic side view of the needle of FIG. 14;

FIG. 19 is a semi-schematic side view of the needle of FIG. 18 rotated 90E about its longitudinal axis;

FIG. 20 is a semi-schematic perspective view of a tool used for assembling one configuration of the present invention;

FIG. 21 is a semi-schematic end view of alternative configuration of the present invention showing the needle guard oriented so as to facilitate insertion within the catheter hub;

FIG. 22 is a semi-schematic end view of the alternative configuration of FIG. 21, showing the needle guard after it has been rotated so as to remain within the catheter hub until the needle is moved to the protected position thereof; and FIG. 23 is a semi-schematic perspective view of an alternative needle guard comprising side flaps and extending arm sections.

DETAILED DESCRIPTION OF THE INVENTION

Figure 13A:
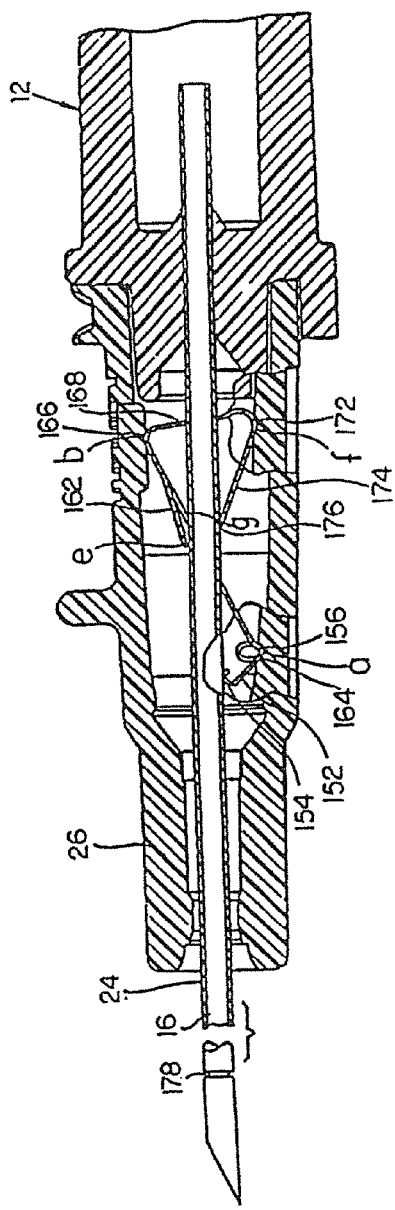
FIGS. 13A and 13B are semi-schematic cross-sectional views of the embodiment of the invention of FIG. 12 in the ready and protected positions, respectively.

The safety IV catheter of the invention, generally designated 10 in the embodiment illustrated in FIGS. 1A and 1B, includes a needle hub 12 that includes an axial opening 14 which securely receives the proximal end of a needle 16 having a sharpened tip 18. The needle hub 12, as is conventional, is hollow and includes a flash chamber 22. As is also conventional, the needle 16 is received within a hollow tubular catheter 24, the proximal end of which is concentrically affixed within the distal end of a catheter hub 26 having a distal section 28 and a contiguous, larger diameter proximal section 30.

The catheter hub 26 terminates at its proximal end in a Luer fitting 32 adapted to receive a tubing set which, in a known manner, administers intravenous fluid into the patient. The catheter 24 is secured within an axial passageway 34 in the distal hub section 28 by means of a sleeve 20 received within the passageway 34, which engages the proximal end of the catheter. Passageway 34 communicates at its proximal end with a flash chamber 36 formed in the hub section 30.

In the ready position of the catheter, shown in FIG. 1A, the distal end of the needle hub 12 is snugly received in the proximal end of the interior of the chamber 36 such that the needle 16 extends through the chamber 36, the passageway 34, and distally beyond the catheter hub 26 and catheter 24, so that its tip extends beyond the tapered distal end of the catheter.

In use, the distal tip of the needle and the catheter are inserted into a patient's vein. Thereafter, the healthcare practitioner manually places the catheter further into the vein and then withdraws the needle by grasping and moving by hand the proximal end of the needle hub 12. The Luer of the catheter hub 26 is then fitted with a source of the fluid that is to be administered into the patient's vein.

In accordance with the present invention, as the needle 16 is being withdrawn from the patient, a protective needle guard 40 located within the hub chamber 36 automatically snaps into a retracted position in which it blocks access to the distal needle tip and prevents further distal movement of the needle tip, thereby to prevent accidental contact by the healthcare practitioner with the needle tip.

As shown in FIGS. 1A and 1B, the needle guard 40 is in the form of a unitary spring clip that is preferably made of a resilient metal such as stainless steel. The spring clip includes a distal arm 42 terminating at its upper end in a curved lip 44 and at its lower end in a pointed end 46 which, in the embodiment of FIG. 1, is received within a mating groove 48 formed in the lower interior wall of the catheter hub section 30.

The spring clip needle guard 40 further includes a transverse segment 50 that extends upward and proximally from the lower pointed end 46 and terminates at a U-shaped upper end 52. In the ready position of the spring clip shown in FIG. 1A, the upper end 52 abuts against the upper interior wall of the catheter hub section 30. The spring clip guard 40 further includes a vertical arm 54 that extends downward from the U-shaped upper end 52 and terminates above the lower wall of the catheter hub section 30. The transverse segment 50 and proximal vertical arm 54, respectively, include axially aligned openings 56, 58 through which the shaft of the needle 16 is free to pass and axially move. The diameter of the opening 58 is slightly greater than that of the needle shaft, whereas the diameter of the opening 56 is greater than that of the opening 58.

In the ready position of the catheter prior to needle withdrawal, the shaft of the needle 16 engages the curved lip 44 of the spring clip needle guard 40, thereby to exert an essentially downward force on the resilient spring clip. That force causes the lower end 46 of the spring clip to seat securely in the groove 48 at point A. That contact, in addition to the abutment of the upper end 52 of the spring clip with the upper interior wall at the catheter hub at point B, securely maintains the spring clip needle guard 40 in the ready position within the catheter hub.

As the needle 16 is retracted to the left, as viewed in FIG. 1A, to its fully retracted position, shown in FIG. 1B, after catheter insertion into the patient's vein, the distal tip of the needle moves proximally past the curved lip 44 of the spring clip needle guard 40 at point C, at which time the downward force previously exerted by the needle shaft on the spring clip is released.

As a result of the needle 16 moving proximally past point C, the retention force on the spring clip needle guard 40 in the catheter hub is released, causing the spring clip needle guard 40 to pivot or snap in a clockwise direction to the retracted position shown in FIG. 1B. As therein shown, distal arm 42 of the needle guard 40 blocks the distal path of the needle 16. Simultaneously with the blocking and releasing actions, the spring clip guard 40 becomes securely clamped onto the needle shaft at points D and E, thereby to securely lock the needle guard 40 onto the needle shaft. At this time, the needle 16 and needle guard 40 can be removed together from the catheter hub 26, and the tip of the needle cannot be pushed past the needle guard because it is blocked by the distal arm 42 and lip 44 of the needle guard.

If desired, a slot 60 may be formed in the needle shaft slightly proximal to the needle tip. When the needle and the needle guard are in their retracted and clamped positions (FIG. 1B), slot 60 is positioned slightly distal to the clamping point E of the transverse segment of the needle guard 40 such that if a subsequent attempt is made to move the needle further in a rearward or proximal direction, the transverse segment 50 at point E will seat into slot 60, thereby to provide an additional force to retain the needle guard 40 on the needle 16 in the protected position in which access to the needle tip is prevented.

The safety IV catheter illustrated in FIGS. 1C and 1D is the same as that illustrated in FIGS. 1A and 1B, except that the slot 60 in the needle shaft in the latter is replaced in the former by a crimp 61 whose width is greater than that of the opening 58 in the vertical arm 54. If an attempt is made to move the protected needle illustrated in FIG. 1C in the rearward or proximal direction, the crimp 61 will engage the wall 54 and will thus not be able to pass through the opening 58, so as to prevent further proximal movement of the needle and removal of the needle from the needle guard, as defined.

The embodiment of the invention illustrated in FIG. 2 is similar to that of FIG. 1 except that, instead of the groove formed in the lower wall of the catheter hub that engages the lower end of the spring clip, a retaining bump 62 is formed in that wall against which the lower end 46 of the needle guard 42 seats when the needle guard 40 is in the ready position, as shown in FIG. 2A.

The embodiment of the invention illustrated in FIGS. 3A and 3B is essentially the same as that of FIG. 2 with the addition of a tether 64 secured at one end to the needle hub 12 and at its other end to the proximal arm 54 of the spring clip needle guard 40. As shown in FIG. 3B, the tether 64 is extended to its full length when the needle hub is retracted to achieve needle removal, so as to more securely retain the needle hub 12 and the spring clip needle guard 40 when the latter is clamped onto the needle when in the retracted position in which, as described above, the distal arm 42 of the spring clip prevents access to the needle tip, and the needle guard 40 and needle are released from the catheter hub.

FIGS. 4A and 4B illustrate a spring clip needle guard embodying the principles of the invention in an alternative configuration. As therein shown, the spring clip needle guard 40a includes a distal arm 65 terminating at its upper end in a curved lip 66 and at its lower end in a U-shaped portion 67 which, in the ready position illustrated in FIG. 4A, contacts a bump 68 formed in the lower inner wall of the catheter hub.

A transverse segment 69 having a central opening 70 extends proximally and upwardly and terminates at an upper U-shaped portion 72. A proximal end wall 74 having an opening 76 depends vertically from portion 72 and then extends distally in a horizontal lower segment 78 which has an opening 80 through which the lower halves of the distal arm 65 and the transverse segment 69 extend in the ready position of the needle guard. Segment 78, at its distal end, extends upwardly at a front wall 82 which has a central opening 84 axially aligned with openings 70, 76. At its upper end, the distal front wall 82 extends in the proximal direction in an upper segment 86 which, as shown in FIG. 4A, contacts the upper inner wall of the catheter hub along substantially its entire length.

As shown in FIG. 4A, when the catheter is in the ready position, the needle shaft passes through openings 70, 76 and 84 and rests on the curved lip 66, urging the arm 65 against the bump 68 in the lower wall of the catheter hub. That engagement, along with the resilient engagement of the upper segment 86 with the upper interior wall of the catheter hub, retains the spring clip 40a in its ready position within the catheter hub.

When the needle hub and needle are retracted to the right, as viewed in FIG. 4A, by a sufficient amount, the needle tip passes below the lip 66 and then releases its downward force on the arm 65. As described above with reference to the first-described embodiment, this release of engagement of the needle shaft and the spring clip arm 65 causes the arm 65 to snap upwards to the retracted position illustrated in FIG. 4B, in which the arm 65 and the lip 66 extend over the needle tip and thereby prevent accidental contact with the needle tip as desired. In this condition, the needle guard is clamped onto the needle shaft in essentially the same manner described above with respect to the first-described embodiment, and the needle and needle guard clamped thereto can be readily removed from the catheter hub, also as described above and as shown in FIG. 4B.

The embodiment of the needle guard illustrated in FIGS. 5A and 5B is essentially the same as that shown in FIGS. 4A and 4B, with the addition of a slot 90 near the distal tip end of the needle. When the needle and needle guard are in their retracted and clamped position (FIG. 5B), the slot 90 is positioned slightly distal to the clamping point of the transverse segment 69 such that if a subsequent attempt is made to move the needle further in a rearward or proximal direction, the transverse segment 69 will seat into the slot 90, thereby to provide an additional force to retain the needle guard in the needle in the protected position in which access to the needle tip is prevented.

The embodiment of the invention illustrated in FIGS. 6A and 6B is the same as that illustrated in FIGS. 4A and 4B, except for the inclusion of a tether 92 secured at one end to the needle hub and at its other end to the proximal wall of the spring clip needle guard. As shown in FIG. 6A, in the ready position, the tether is wound around the distal end of the needle hub. As shown in FIG. 6B, when the needle and needle guard are in their retracted position, the tether is extended to its full length and aids in the retention of the needle guard to the needle hub. If desired, the embodiment of the invention embodiment illustrated in FIGS. 6A and 6B could also include a needle slot as in the embodiment of the invention illustrated in FIGS. 5A and 5B.

The embodiment of FIGS. 7A-7C differs from the previously described embodiments primarily with regard to the construction and operation of the spring clip needle guard 96. As shown in FIGS. 8 and 9, the spring clip 96 includes a central transverse section 98 which includes a central slot 100. A sloping section 102 extends from section 98 in the proximal direction and terminates at a curved end 104 from which a proximal vertical arm 106 extends. The arm 106 terminates at its lower end in a U-shaped section 108. The distal end of the transverse section 98 terminates in a curved section 110 from which a vertical proximal arm 112 extends. The distal arm 112 terminates at its upper end in a curved arm 114.

A cutout portion in section 98 defines a flexible flap 116 which terminates at its distal free end in a downwardly sloping locking tab 18. As in the prior embodiments, the proximal arm 106 includes an opening 58.

As shown in FIG. 7A, the spring clip needle guard 96, when in the ready position illustrated therein, is inserted within the catheter hub 26 so as to allow the needle 16 to pass through the opening 58 and slot 100. As in the previously described embodiments, the curved end 104 abuts against the inner upper wall of the catheter hub 26 at point B, and the curved section 110 seats within the mating groove 48 at point A formed in the lower inner wall of the catheter hub. In addition, the lower curved section 108 contacts at point F the lower inner wall of the catheter hub 26 at a location proximal to point B.

In operation, the needle is initially withdrawn into the catheter hub until it reaches the tab engaged position illustrated in FIG. 7B in which, as therein shown, the locking tab 118 is received within the needle groove or slot 60. At this point, the spring clip remains in contact with the inner wall of the catheter hub at points A, B and F, while the needle tip 18 engages the curved end 114, thereby to urge section 110 into the groove 48 at point C. The relative position of point F with respect to point B prevents the needle and clip from being prematurely released from the catheter hub by preventing the distal end of the clip from tipping upwards and the proximal end from slipping downward with the clip in the tab engaged position shown in FIG. 7B.

As the needle is withdrawn further away from the patient, as shown in FIG. 7C, the needle tip passes beyond the curved end 114, thereby releasing the downward force that had been previously exerted on the curved end 114 by the needle.

This sudden release of the downward force on the spring clip end causes the distal end of the spring clip 96 to pivot upward so that the distal end 112 of the spring clip 96 moves rapidly to a position in which it prevents or blocks the motion of the needle in the distal direction. The spring clip 96 is retained on the needle 16 and will be removed from the catheter hub 26 when the needle is completely removed. Movement of the spring clip 96 from its protecting or retracted position shown in FIG. 7C is further prevented by the insertion of the locking tab 118 into the needle groove 60, which prevents the spring clip from rotating around the periphery of the needle. This, in turn, secures the spring clip on the needle, even if the clip were subjected to a twisting and pulling force.

The safety IV catheter illustrated in FIGS. 7D and 7E is the same s that illustrated in FIGS. 7A and 7B, except that the slot 60 in the needle shaft in the latter is replaced in the former by a crimp 61 whose width is greater than that of the opening 58 in the vertical arm 54. If an attempt is made to move the protected needle illustrated in FIG. 7D in the rearward or proximal direction, the crimp 61 will engage the wall 54 and will not be able to pass through the opening 58, so as to prevent any further proximal movement of the needle and removal of the needle from the needle, as desired.

The embodiment of the spring clip needle guard 120 disclosed in FIGS. 10A, 10B, and 11 comprises first and second arms 122 and 124, respectively, joined at their proximal ends in a hinged arrangement at 125 to the ends of a rear wall 126. The distal ends of the arms 122, 124 each include a curved protrusion 128 extending to a distal end wall 130, which, in turn, terminates in a lip 132. As seen best in FIG. 11, the rear wall 126 includes a central opening 134, and the arms 122 and 124 each include a narrow portion 142 that extends between a distal wide portion 140 and a proximal wide portion 144. A lateral clamping edge 146 is defined at the distal wide portion 144.

As shown in FIG. 10A, when the needle guard 120 is in its ready position, the curved protrusions 128 in each of the arms 122, 124 are received in an annular groove or ring 136 formed in the inner wall of the catheter hub 26 which, as in the prior embodiments, is removably fit into the distal end of a needle hub 12. Also as in the prior embodiment, a needle 16 having a sharpened tip 18 at its distal end is received within a tubular catheter 24 which is secured t the distal end of the catheter hub 26. The proximal end of the needle 16 passes through the opening 134 in the rear wall 126. The needle 16 includes an crimp 138 which is sufficiently small to allow the needle 16 to move axially along the catheter 24 but is greater in width than the opening 134 for reasons to be described below.

In the ready position illustrated in FIG. 10A, the needle shaft passes through the needle guard and applies an outward radial force on the resilient arms 122, 124 by means of its engagement with the lips 132, so as to urge the curved protrusions 128 of each of the arms into the annular groove 136, so as to retain the needle guard 120 in a fixed position within the inner wall of the catheter hub 26. The shaft of a needle 16 that passes through the needle guard 120 frictionally engages the inner edges of the narrow portion 142 of arms 122, 124 so as to further retain the needle in its ready position.

When the needle is retracted axially to the right, as viewed in FIG. 10A, within the catheter hub and moves past the end lip 132 of the needle guard, the radial force previously exerted on the arms 122, 124 of the needle guard 120 is suddenly released. This causes the distal end walls 130 of the needle guard to be released from their seat in the annular groove 136 and to pivot inward into the catheter hub until, as seen in FIG. 10B, the end walls 130 overlap one another at a location distally in front of the needle tip, thereby to form a barrier that prevents inadvertent contact with, and distal movement of, the needle tip. At the same time, the clamping edges 146 of the needle guard are urged against the needle tip to restrict further axial movement of the needle.

As also shown in FIG. 10B, the needle guard 120 and the needle clamped to the needle guard after needle retraction can be removed from the catheter hub as a unitary assembly and safely discarded. If an attempt is made, intentionally or inadvertently, to pull the needle further to the right, as shown in FIG. 10B, out of the needle guard, the crimp 138 on the needle shaft will come into contact with the end wall 126, and, since its width is greater than that of the opening 134, the end wall 126 will at this point prevent any further axial movement of the needle out of the needle guard.

Figure 13B:
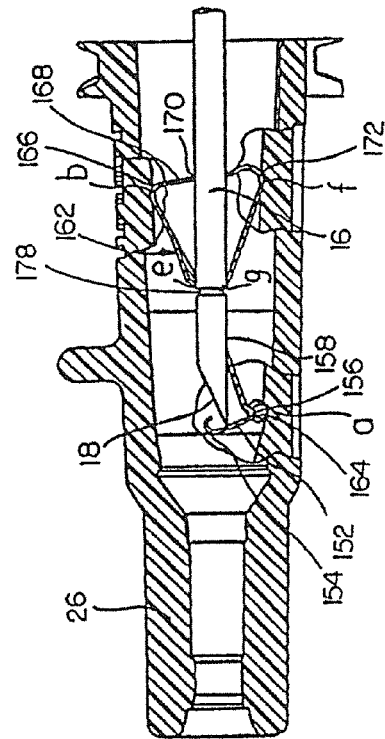
Figure 12:
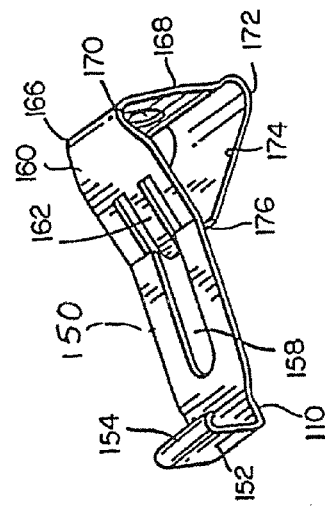
FIG. 12 is a semi-schematic perspective view of a safety IV catheter in accordance with another embodiment of the invention.

This spring clip guard of the invention, in the embodiment illustrated in FIGS. 12, 13A and 13B, includes a transverse arm 150 terminating at its distal end at a distal end wall 152, which includes at its upper end a curved lip 154 and at its lower end a curved end 156. An elongated rectangular opening or slot 158 is provided in the transverse arm 150. The proximal ends of the transfer arm 150 and the opening 158 terminate at an extension 160 extending upwardly at an angle from the arm 150 and having a finger or flap 162 that extends toward the opening 158.

The proximal end of the extension 160 terminates t a curved end 166 from which a proximal end wall 168 extends downwardly. The wall 168, which includes an opening 170, terminates at its lower end at a curved section 172 from which extends an upwardly sloping arm 174 that terminates at a clamping edge 176. As can be seen in FIGS. 13A and 13B, a 360E circular groove 178 is formed about the circumferential wall of the needle 16 slightly inwardly from the tip 18 of the needle.

In the ready position of the spring clip guard of FIG. 12, as illustrated in FIG. 13A, the shaft of the needle passes through the aligned opening 170 in the rear wall 168 and the opening 158 in the transverse arm 150 and extends distally beyond the catheter hub. As in the prior embodiments described hereinabove, the needle shaft in this position exerts a downward radial force on the arm 150 by means of its engagement with the curved lip 154. This downward force urges the curved end 156 of the spring clip to seat firmly within a groove 164 formed in the inner wall of the catheter hub at point A.

At the same time, the upper curved end 166 of the end wall 168 engages the inner wall of the catheter hub at point B, and the lower curved end 172 of the wall 168 engages the inner wall of the catheter hub at point F. Further engagement between the needle shaft and the spring clip is provided by the contact of the finger 162 with the upper end of the needle shaft at point E and between the clamping edge 176 and the lower surface of the needle shaft at point G. In this manner, the needle is securely but movably retained within the catheter hub in its ready position.

When the needle is retracted axially to the right, as viewed in FIGS. 13A and 13B, it eventually moves past its engagement with the lip 154, thereby to suddenly release the radial force it had previously exerted on the arm 150 of the needle guard. This release of engagement between the needle shaft and the lip 154 allows the distal curved end 156 of the distal end wall 152 of the spring clip to be released from its seat in the annular groove 164 so that the arm 150 and the end wall 152 pivot quickly into the interior of the catheter hub, as seen in FIG. 13B, to a position at which the wall 152 forms a barrier to the needle tip. This positioning of the wall 15 prevents inadvertent contact with the needle tip. The engagement of the finger 162 and the clamping edge 176 to the opposing sides of the needle prevents further axial movement of the needle in either direction.

If an attempt is thereafter made to pull the needle axially further to the right, as viewed in FIG. 13B, the finger 162 will enter the circular groove 178 formed in the needle surface, thereby to prevent further axial movement of the needle in the proximal direction out of the needle guard.

As shown in FIG. 14, yet a further embodiment of the present invention is generally similar to the embodiment shown in FIG. 10A, with the notable exception that the annular groove or ring 136 of the embodiment shown in FIG. 10A has been replaced with an inwardly extending annular protrusion 136a which serves an analogous function with respect to the annular groove or ring 136. Preferably, the annular protrusion 136a extends completely around the interior of the catheter hub 26 in a generally continuous ring-like fashion.

The annular protrusion 136a removably retains the needle guard 120 within the catheter hub 26 as the needle 16 is withdrawn from the catheter hub 26, until the arms 122, 124 of the needle guard 120 move inwardly as the tip 18 of the needle 16 moves past the end lips 132 of the needle guard 120, as discussed in detail above.

Although the annular protrusion 136a is shown in FIG. 14 as having a generally semi-circular cross-section, those skilled in the art will appreciate that various other cross-sectional configurations of the annular protrusion 136a are likewise suitable. For example, the annular protrusion 136a may alternatively have a generally triangular, square, rectangular, or any other desired cross-sectional configuration.

The annular protrusion 136a is preferably formed integrally with respect to the catheter hub 26, such as being injection molded as a portion thereof. Alternatively, the annular protrusion 136a may be formed separately from the catheter hub 26 and attached to the catheter hub 26 via adhesive bonding, ultrasonic welding or any other desired method.

Moreover, it will be appreciated that the annular protrusion 136a may have any desired configuration which releasably retains the needle guard 120 within the catheter hub 26 until the tip 18 of the needle 16 has been withdrawn past the lips 132 of the needle guard 120.

As shown in FIGS. 14 and 15, when the needle guard 120 is in its ready position, the curved protrusions 128 in each of the arms 122, 124 are positioned near, e.g., in abutting contact with, the annular protrusion 136a formed on the inner wall of the catheter hub 26 which, as in the prior embodiments, is removably fit onto the distal end of a needle hub 12. Also, as in the prior embodiment, a needle 16 having a sharpened tip 18 at its distal end is received within a tubular catheter 24 which is secured to the distal end of the catheter hub 26. The proximal end of the needle 16 passes through the opening 134 in the rear wall 126 of the needle guard 120. The needle 16 includes an crimp 138 which is sufficiently small to allow the needle 16 to move axially along the catheter 24 but which is greater in width than the opening 134 for reasons to be described below.

In the ready position illustrated in FIGS. 14 and 15, the needle shaft passes through the needle guard 120 and applies an outward radial force on the resilient arms 122, 124 by means of its engagement with the lips 132, so as to urge the curved protrusions 128 of each of the arms against the inner wall of the catheter hub 26, so as to retain the needle guard 120 in a fixed position within the catheter hub 26. As was the case with the embodiment described with respect to FIGS. 10A and 10B, the shaft of a needle 16 that passes through the needle guard 120 and optionally frictionally engages the inner edges of the narrow portion 142 (shown in FIG. 11) of arms 122, 124 so as to further retain the needle in its ready position.

When the needle is retracted axially to the right, as viewed in FIG. 14, and moves past the end lips 132 of the needle guard 120, the radial force previously exerted on the needle guard arms 122, 124 is suddenly released. The annular protrusion 136a prohibits movement of the needle guard 120 to the right as the needle 16 moves to the right, until the tip 18 past the end lips 132 of the needle guard 120. Movement of the tip 18 past the end lips 132 allows the resilient arms 122, 124 and their protrusions 128 therein to move inwardly a sufficient distance to cease abutting the annular protrusion 136a. As was the case with the embodiment described with regard to FIGS. 10A and 10B, the distal end walls pivot inward into the catheter hub until the end walls overlap one another at a location distally in front of the needle tip, thereby to form a barrier that prevents inadvertent contact with, and distal movement of, the sharpened needle tip 18. At the same time, the clamping edges 146 of the needle guard (as described with respect to FIG. 11) are optionally urged against the needle 16 to restrict further axial movement of the needle, in relation to the needle guard 120.

As again shown in FIG. 10B (which shows the needle 16 and the needle guard 120 removed from the catheter hub 26 and is thus applicable to both the embodiment of FIG. 10A and the embodiment of FIG. 14), the needle guard 120 is fixedly attached to the needle 16 after needle retraction, such that the needle guard and the needle can be removed from the catheter hub as a unitary assembly and safely discarded. If an attempt is made, either intentionally or inadvertently, to pull the needle further to the right (as viewed in FIG. 10B) out of the needle guard, the crimp 138 on the needle shaft will come into contact with the end wall 126, and, since the crimp width is greater than the diameter of the opening 134, the end wall 126 will, at this point, prevent any further axial movement of the needle out of the needle guard.

As shown in FIG. 16, the inwardly extending, generally annular protrusion 136b may alternatively be formed to have a generally C-shaped configuration. Optionally, the C-shaped protrusion 136b may be defined by a metal snap ring which is partially disposed within a groove, such as groove 136 of FIG. 10a. Thus, the inwardly extending, generally annular protrusion 136b may be formed by sliding a metal snap ring into the catheter hub 26 until the metal snap ring snaps into a groove formed within the catheter hub 26.

As shown in FIG. 17, as a further alternative the inwardly extending, generally annular protrusion 136c may be defined so as to have two generally semi-circular segments or portions. Indeed, those skilled in the art will appreciate that various different configurations of the inwardly extending, generally annular protrusion are likewise suitable.

Thus, the inwardly extending, generally annular protrusion may have any desired configuration. It is preferred that the inwardly extending, generally annular protrusion not have any gap(s) 137 (as shown in FIGS. 16 and 17) which have a width greater than the width of the distal end walls 130 of the needle guard 120. Sizing the gaps 137 so as to be smaller than the width of the end walls tends to prevent the needle guard 120 from passing through such gaps 137 and thereby undesirably allowing the needle guard 120 to slip out of the needle hub 26 without properly protecting the tip 18 of the needle 16. Thus, according to the present invention, any desired number of separate sections may be utilized to define the inwardly extending, generally annular protrusion, as long as the needle guard 120 is effectively held in place thereby as the needle 14 is withdrawn from the catheter 24.

As shown in FIGS. 18 and 19, the crimp 138 formed in the needle 16 preferably defines a pair of generally opposed, outwardly extending bulges 138a in the needle and also defines a pair of generally opposed, inwardly extending depressions 138b, which are disposed generally orthogonally with respect to the bulges 138a. The bulges 138a define a crimp 138 having a width, dimension W, which is small enough to facilitate movement of the needle 16 within the catheter 24, as shown in FIG. 14, and which is too large to pass through the central opening 134 formed in the end wall 126 of the needle guard 120, as discussed above.

The crimp 138 may be formed by any contemporary crimping process, such as those processes wherein two jaws of a vise or crimper come together so as to squeeze the needle 16 in a manner which forms the depressions 138b of FIG. 19, thereby consequently also forming the bulges 138a.

The IV catheter shown in FIG. 14 is assembled by sliding the needle guard 120 over the sharpened tip 18 of the needle 16 before the crimp 138 is formed in the needle 16. The needle 16 passes through the opening 134 formed in the end wall 126 of the needle guard 120. The distal arms 132 are opened and the needle 16 passes through them. Next, the crimp 138 is formed in the needle 16, so that the needle guard 120 is captured between the crimp 138 and the needle hub 12.

Next, the needle 16, having the needle guard 120 thereon, is slid into the catheter hub 26 such that the sharpened tip 18 of the needle 16 enters the catheter 24. The needle 16 is slid into the catheter 24 until the curved protrusions 128 of the needle guard 120 abut the annular protrusion 136A.

Once the curved protrusions 128 abut the annular protrusion 136A, the needle guard 120 ceases to move along with the needle 16. The needle guard 120 may cease to move along with the needle 16 before the curved protrusions 128 of the needle guard 120 abut the annular protrusion 136A, since the inner surface of the catheter hub 26 tapers inwardly, such that the inside diameter thereof is reduced as the needle guard 120 travels further into the catheter hub 26. Thus, the needle guard 120 may cease moving along with the needle 16 due to such narrowing of the inside of the needle guard 26, when the inside diameter of the catheter hub 26 becomes too small for the needle guard 120 to pass further therethrough.

Once the needle guard 120 has ceased to move along with the needle 16 as the needle is inserted into the catheter 24, a tool is used to gently urge the needle guard 120 further into the catheter hub 26, until the curved protrusions 128 of the needle guard 120 pass beyond the annular protrusion 136A. Sufficient force must be applied to the needle guard 120 via the tool so as to cause the curved protrusions of the needle guard 120 to flex toward one another such that they pass beyond the annular protrusion 136A.

After the curved protrusions 128 of the needle guard 120 have passed beyond the annular protrusion 136A and have flexed back outwardly, generally so as to contact the inner wall of the catheter hub 26, then the needle guard 120 is in the ready position as shown in FIG. 14.

The tool used to urge the needle guard 120 past the annular protrusion 136 within the catheter hub 26 may comprise any convenient structure suitable for such use. For example, as shown in FIG. 20, a simple pin 200 with a slot 202 running the length thereof (so as to receive the needle 16 as the needle guard 120 is pushed) may suffice.

Thus, when the IV catheter of the present invention is assembled, the curved protrusions 128 of the needle guard 120 positively engage the inwardly extending annular protrusion 136A such that the needle guard 120 remains within the catheter hub 26 as the needle 16 is withdrawn from the catheter 24, until the sharpened tip 18 of the needle passes between the lips 132 of the needle guard 120 so as to disengage the curved protrusions 128 with respect to the annular protrusion 136A to allow the needle guard 120 to move out of the catheter hub 26 along with the needle 16.

An alternative method for assembling the spring clip safety I.V. catheter of the present invention may be utilized when the annular protrusion is configured as a C-shaped protrusion or an open ring 136b, as shown in FIG. 16 and is formed separately from the catheter hub 26. In this instance, the open ring 136b can be placed upon the needle guard 120 (between the proximal and distal ends thereof) after the needle 16 has been passed through the needle guard 120 and crimped. Then, both the needle guard 120 and the open ring 136b may be simultaneously pushed into the catheter hub 26 utilizing the same tool.

This tool preferably has at least two fingers, one of which extends along each side of the needle guard 120, so as to push the open ring 136b further into the catheter hub 26 than the proximal end of the needle guard 120. In this manner, the needle guard 120 does not have to be pushed over the annular protrusion 136. Rather, the needle guard 120 and the annular protrusion 136b are assembled together, i.e., along with one another. The annular protrusion 136b is thus assembled into the catheter hub 26 so as to lock the needle guard 120 into position, where the needle guard 120 remains until the needle 16 is moved to the protective position thereof, as discussed in detail above.

Referring now to FIGS. 21 and 22, yet a further alternative method for assembling the needle guard 120a into the catheter hub 26 is shown. According to this alternative method, the annular protrusion 136d is configured so as to have at least four openings 137 formed therein and is configured so that the needle guard 120a may pass through the openings 137 utilizing very little or no insertion force. After the needle guard 120a has been pushed into the catheter hub 26 past the annular protrusion 136d, then the needle guard 120a is rotated so as to position the four corners 250 thereof behind the annular protrusion 136d as shown in FIG. 22, which then functions so as to maintain the needle guard 120a with the catheter hub 26 until the needle 16 is withdrawn and moved into the protective position thereof, as discussed in detail above.

It may be desirable to form the needle guard 120a so as to provide a generally square profile, as shown in FIGS. 21 and 22. However, as those skilled in the art will appreciate, various different generally square, rectangular or other profiles of the needle guard 120a are likewise suitable. It is merely necessary to locate the openings 137 formed in the annular protrusion 136d such that the needle guard 120a is readily received therebetween during the assemble process and is then held in place thereby, after rotating the needle guard 120a so as to place the corners 250 thereof into abutting contact with the annular protrusion 136d.

Referring now to FIG. 23, a semi-schematic perspective view of an alternative protector clip or spring clip needle guard 182 provided in accordance with aspects of the present invention is shown. The protector clip 182 is similar to the needle guards described above with a few changes and may be used with the needle assemblies described above. In one exemplary embodiment, the first arm 184 and the second arm 186 each incorporates an arm extension member 188 adjacent an edge 190 of the respective arms. Preferably, the arm extension members 188 of the two arms project inwardly from a first arm surface 192 of the respective arms 184, 186 in the direction of the needle, assuming that one passes through the central opening 134 of the rear wall 126. Alternatively, the arm extension members 188 may project outwardly from the second arm surface 194 away from the needle. Because the two arms 184, 188 cross one another, as shown, there may be sections of the arm extension members 188 that project in the direction of the needle while other portions project away from the needle.

In one exemplary embodiment, the arm extension members 188 comprise a flap or a wing stamped from a metal sheet, such as a stainless steel sheet, as part of forming the protective clip 182 and bent either inwardly towards the needle or outwardly away from the needle. The arm extension members 188 have a length that can vary. In one exemplary embodiment, the length of the arm extension members extend a substantial length of the first and second arms 184, 186. More particularly, the arm extension members extend from approximately just distal of the hinged section 125 to approximately just distal of the proximal wide portion 144. However, the length can also extend longer or short than as described. For example, in one exemplary embodiment, the arm extension members 188 can have a length approximately the length of the narrow portions 142 of the first arm 184 and the second arm 186. Although not required, the ends 196 of the arm extension members 188 may be tapered to eliminated sharp edges. In an alternative embodiment, the arm extension members 188 may be eliminated entirely or formed on only one of the first or the second arm.

In one exemplary embodiment, two side flaps 198 project inwardly in the direction of the needle are formed on the finger or lip 132 of the second arm 186. Similar to the arm extension members 188, the side flaps 198 are formed when forming or stamping a sheet of metal for the protector clip 182 and bent inwardly in the direction of the needle. The side flaps 198 each comprises a top section 200 and two sides 202, 204. Although the sides 204 furthest proximal of the distal wall terminate evenly with the edge 206 of the lip 132, the side flaps 198 may be shifted distally and the edges 204, 206 offset. The side flaps 198 should be of sufficient size to delimit the needle from moving away or outside the space defined by the two side flaps upon activation of the protective clip 182 over the needle tip.

In an alternative embodiment, the finger or lip 132 of the first arm 184 may incorporate the side flaps 198 instead of the finger or lip 132 of the second arm 186. Still alternatively, both fingers or lips 132 of the first arm 184 and the second arm 186 may incorporate side flaps for a total of four side flaps.

It will thus be appreciated that the spring clip needle guard of the invention as employed in an IV catheter provides automatic and reliable protection of the needle tip upon needle retraction to prevent accidental contact with the needle tip by a healthcare practitioner It will also be appreciated that modifications may be made to the embodiments of the invention specifically described hereinabove without necessarily departing from the spirit and scope of the invention.

What is claimed is:

1. An IV catheter apparatus comprising:
   a catheter hub having a catheter tube extending distally thereof;
   a needle hub having a needle with a shaft having an irregularly configured portion on the needle shaft slightly proximal of a needle tip, the shaft extending distally of the needle hub and extending through the catheter hub and the catheter tube with the needle tip extending beyond the catheter tube;
   a needle guard disposed within the catheter hub and having a ready position in which the needle guard is positioned proximally of the needle tip and a protective position in which the needle guard blocks the needle tip, the needle guard having at least one resiliently movable arm that is urged radially in the ready position by the shaft; and
   a shoulder disposed within the catheter hub holding the needle guard in the catheter hub in the ready position;
   wherein the needle guard has a wall proximal and transverse of the at least one resilient movable arm and through which the needle shaft passes, and a perimeter defining an opening associated with the wall to engage the irregularly configured portion after a portion of the needle shaft, which is proximal of the irregularly configured portion, is retracted through the perimeter to draw the needle guard proximally with the needle tip blocked.

2. The IV catheter apparatus of claim 1, wherein the at least one resilient movable arm extends distally of the wall.

3. The IV catheter apparatus of claim 1, wherein the at least one resilient movable arm further includes a radially extending member that moves radially to block the needle tip when in the protective position.

4. The IV catheter apparatus of claim 3, wherein the radially extending member is a guard wall that terminates in a lip engaging the shaft of the needle in the ready position.

5. The IV catheter apparatus of claim 4, wherein the needle urges the at least one resilient movable arm radially outwardly against the shoulder to hold the needle guard in the ready to use position.

6. The IV catheter apparatus of claim 1, further comprising a second resilient movable arm spaced from the at least one resilient movable arm.

7. The IV catheter apparatus of claim 1, wherein the irregularly configured portion has a larger outer dimension than the perimeter defining the opening.

8. The IV catheter apparatus of claim 1, wherein the irregularly configured portion is a crimped section of the needle shaft which increases the width of the needle in one direction.

9. The IV catheter apparatus of claim 6, wherein the second resilient movable arm and the at least one resilient movable arm have distal ends with each distal end including a curved protrusion extending to a guard wall.

10. The IV catheter apparatus of claim 9, wherein the curved protrusions are received against the shoulder.

11. The IV catheter apparatus of claim 1, wherein the shoulder is part of an annular groove or ring formed in an inner wall of the catheter hub.

12. The IV catheter apparatus of claim 1, wherein the second resilient movable arm and the at least one resilient movable arm intersect.

13. The IV catheter assembly of claim 1, wherein the needle guard is unitary.

14. An IV catheter apparatus comprising:
   a tubular catheter having a proximal end and a distal end;
   a needle having a needle shaft, a needle crimp, and a tip and wherein the needle is attached to a distal end of a needle hub, said needle being received within said tubular catheter when the needle is in a ready position;
   a catheter hub attached to the proximal end of said tubular catheter, said catheter hub having a hollow interior and an inner wall, said needle being movable between said ready position in which said tip is outside of said catheter hub and a retracted position in which said tip is within said catheter hub;
   a needle guard positioned in the interior of said catheter hub, wherein the needle guard has a resilient portion having an end wall engaged by said needle shaft when said needle is in the ready position, the end wall of the needle guard resilient portion being movable within the interior of said catheter hub to a blocking position distal of said needle tip when said needle is in the retracted position in which said needle shaft no longer exerts a force on said end wall of the resilient portion of said needle guard;
   wherein the needle guard is retained in the catheter hub by a projection formed on the inner wall of the hollow interior when the end wall of the resilient portion is abutted by a side of the needle shaft and biased radially outwardly; and
   wherein the needle guard prevents accidental, inadvertent contact with the needle tip when the needle is in the retracted position by a portion of a proximal end of the needle guard making contact with the needle crimp and the end wall of the resilient portion blocking the needle tip.

15. The IV catheter apparatus of claim 14, wherein the resilient portion is an arm extending distally from the proximal end of the needle guard to the end wall.

16. The IV catheter apparatus of claim 15, wherein the needle guard has a second arm.

17. The IV catheter apparatus of claim 16, wherein when in the ready position the needle urges the arm and the second arm away from each other and against the inner wall of the catheter hub.

18. The IV catheter apparatus of claim 15, wherein the arm extending distally from the proximal end is joined to the proximal end in a hinged arrangement.

19. The IV catheter apparatus of claim 15, wherein a distal end of the arm has a curved protrusion extending to the end wall of the resilient portion.

20. The IV catheter apparatus of claim 14, wherein the projection is an annular ring.

21. An IV catheter apparatus comprising:
- a catheter tube having a proximal end and a distal end;
- a catheter hub having a hollow interior with a projection, a proximal end and a distal end, the catheter hub being connected to the proximal end of the catheter tube;
- a needle having a proximal end, a distal end, a needle shaft, a needle tip at the distal end of the needle shaft, and laterally extending bulges;
- a needle hub having a proximal end and a distal end, the needle being attached to the distal end of the needle hub;
- a needle guard including a proximal end wall having an opening therein and first and second arms extending distally from the proximal end wall, the first arm including an end wall which is biased radially outwardly by the needle shaft; and
- wherein in a ready position of the needle, the needle shaft extends through the opening in said proximal end wall and through the catheter tube so that the needle tip extends out of the distal end of the catheter tube and the needle guard is retained within the hollow interior of the catheter hub by engagement of part of the first arm with said projection; and
- wherein in a retracted position of the needle, the needle is moved in a proximal direction relative to the catheter hub until the needle tip is inside the catheter hub and the end wall of the first arm is no longer biased radially outwardly by the needle shaft whereby said first arm separates from the projection so that the needle guard can move proximally past the projection when the bulges of the needle engage the proximal end wall of the needle guard thereby preventing further proximal movement of the needle relative to the needle guard and wherein the end wall of the first arm protects the needle tip against insertion into objects or persons.

22. The IV catheter apparatus as claimed in claim 21, wherein the end wall of the first arm is generally orthogonal to the first arm.

23. The IV catheter device as claimed in claim 21, wherein the proximal end wall, the first and second arms, and the end wall of the first arm of the needle guard are unitary.

24. The IV catheter as claimed in claim 23, wherein the needle guard is formed from resilient material.

25. The IV catheter as claimed in claim 21, wherein the laterally extending bulges are formed by deformation of the needle shaft.

* * * * *

UNITED STATES PATENT AND TRADEMARK OFFICE
CERTIFICATE OF CORRECTION

PATENT NO. : 9,289,237 B2
APPLICATION NO. : 14/160349
DATED : March 22, 2016
INVENTOR(S) : Kevin Woehr et al.

Page 1 of 1

It is certified that error appears in the above-identified patent and that said Letters Patent is hereby corrected as shown below:

On the Title page, in item (72), in column 1, in "Inventors", line 3, delete "Coopersberg" and insert -- Coopersburg --, therefor.

On the Title page 3, in column 1, item (56), under "Other Publications", line 66, delete "Termuno;" and insert -- Terumo; --, therefor.

In the Specification

In column 8, line 61, delete "same s" and insert -- same as --, therefor.

In column 10, line 4, delete "t" and insert -- at --, therefor.

In column 13, line 51, delete "I.V." and insert -- IV --, therefor.

In the Claims

In column 16, line 27, in claim 13, delete "assembly" and insert -- apparatus --, therefor.

In column 18, line 21, in claim 23, delete "device" and insert -- apparatus --, therefor.

In column 18, line 24, in claim 24, delete "catheter" and insert -- catheter apparatus --, therefor.

In column 18, line 26, in claim 25, delete "catheter" and insert -- catheter apparatus --, therefor.

Signed and Sealed this
Second Day of August, 2016

Michelle K. Lee
*Director of the United States Patent and Trademark Office*